(12) United States Patent
Daffinson et al.

(10) Patent No.: US 11,026,812 B2
(45) Date of Patent: Jun. 8, 2021

(54) INTERVERTEBRAL IMPLANT DEVICE WITH LORDOTIC EXPANSION

(71) Applicant: Amendia, Inc., Marietta, GA (US)

(72) Inventors: Brion Daffinson, Marietta, GA (US); Austin Howell, Decatur, GA (US); Chase Thornburg, Cumming, GA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 16/158,622

(22) Filed: Oct. 12, 2018

(65) Prior Publication Data
US 2019/0038435 A1    Feb. 7, 2019

Related U.S. Application Data

(60) Continuation of application No. 15/938,083, filed on Mar. 28, 2018, now Pat. No. 10,166,117, which is a
(Continued)

(51) Int. Cl.
| *A61F 2/44* | (2006.01) |
| *A61F 2/46* | (2006.01) |
| *A61B 17/70* | (2006.01) |
| *A61B 17/80* | (2006.01) |
| *A61F 2/30* | (2006.01) |

(52) U.S. Cl.
CPC ........ *A61F 2/4611* (2013.01); *A61B 17/7059* (2013.01); *A61B 17/8042* (2013.01); *A61B 17/8057* (2013.01); *A61F 2/447* (2013.01); *A61F 2/30749* (2013.01); *A61F 2002/3054* (2013.01); *A61F 2002/30261* (2013.01); *A61F 2002/30265* (2013.01); *A61F 2002/30383* (2013.01); *A61F 2002/30411* (2013.01); *A61F 2002/30471* (2013.01); *A61F 2002/30507* (2013.01); *A61F 2002/30538* (2013.01); *A61F 2002/30556* (2013.01);
(Continued)

(58) Field of Classification Search
CPC ................................................ A61F 2/44–447
See application file for complete search history.

(56) References Cited

U.S. PATENT DOCUMENTS

| 8,366,777 B2 | 2/2013 | Matthis et al. |
| 8,628,578 B2 | 1/2014 | Miller et al. |

(Continued)

FOREIGN PATENT DOCUMENTS

| WO | 2016051095 | 4/2016 |
| WO | 2016183382 | 11/2016 |

*Primary Examiner* — Nicholas J Plionis

(57) ABSTRACT

An expandable interbody fusion implant device has a frame, two ramp assemblies, a threaded drive shaft and at least one base plate, preferably two. The frame has a first lateral side and a second lateral side and a distal end and a proximal end. Each ramp assembly has a translating ramp with a threaded opening, a first pivoting hinged ramp and a second pivoting hinged ramp. Each base plate is hinged to a first lateral side of the frame. Each base plate is hinged to the distal ramp assembly and the proximal ramp assembly at an end of one of said pivoting hinged ramps of each ramp assembly. The drive shaft has a distal drive shaft component having threads for translating the distal ramp assembly and a proximal drive shaft component having threads for translating the proximal ramp assembly.

11 Claims, 19 Drawing Sheets

Related U.S. Application Data division of application No. 15/635,657, filed on Jun. 28, 2017, now Pat. No. 9,962,272.

(52) U.S. Cl.
CPC ............... *A61F 2002/30578* (2013.01); *A61F 2002/30593* (2013.01); *A61F 2002/4627* (2013.01)

(56) References Cited

U.S. PATENT DOCUMENTS

| | | |
|---|---|---|
| 8,795,366 B2 | 8/2014 | Varela |
| 9,005,291 B2 | 4/2015 | Loebl et al. |
| 9,204,974 B2 | 12/2015 | Glerum et al. |
| 9,414,936 B2 | 8/2016 | Miller et al. |
| 9,962,272 B1 * | 5/2018 | Daffinson .............. A61F 2/4611 |
| 2010/0211176 A1 | 8/2010 | Greenhalgh |
| 2013/0023994 A1 | 1/2013 | Glerum |
| 2013/0297029 A1 | 11/2013 | Kana et al. |
| 2016/0089247 A1 | 3/2016 | Nichols et al. |
| 2016/0250034 A1 | 9/2016 | Loebl et al. |
| 2017/0042695 A1 | 2/2017 | Foley et al. |
| 2017/0100255 A1 | 4/2017 | Hleihil et al. |
| 2017/0296352 A1 | 10/2017 | Richerme et al. |

\* cited by examiner

INTERVERTEBRAL IMPLANT DEVICE WITH LORDOTIC EXPANSION

The present invention is a continuation of U.S. application Ser. No. 15/938,083 filed on Mar. 28, 2018, which is a division of U.S. application Ser. No. 15/635,657 filed Jun. 28, 2017, now U.S. Pat. No. 9,962,272 issued May 8, 2018, entitled, "Intervertebral Implant Device With Lordotic Expansion".

TECHNICAL FIELD

The present disclosure relates to an expandable interbody fusion implant device with lordotic expansion and contraction for implantation between vertebral bodies.

BACKGROUND OF THE INVENTION

Spinal stabilization can be achieved by providing an interbody implant. Some of these implants are bone, PEEK (polyether ether ketone), solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to retain the implant in place.

It has been found desirable to keep the surgical opening as small as practical while still having sufficient room to insert the implant device and the end of an elongated tool or insertion instrument.

Advantageously, if the implant size could be reduced further that would allow the surgical opening to be reduced; however, once implanted the device needs to be expandable to provide sufficient spacing of the vertebrae.

A whole class of expandable interbody implant devices have been developed for this purpose. Some prior art devices use hydraulic expansion or inflatable balloons. Some devices are stackable elements piled on themselves to raise their height. Some use rotatable screw jack designs. Some are wedges that have a fixed hinged end and an opposite expandable end. Most of the rotatable expandable devices using screw threads require the device to be round cylinders or posts.

One of the problems of such devices is the amount of post insertion manipulation required to reach a fully expanded properly space height is tedious and time consuming Secondly, additional set screws or locking elements are often required to keep the device at its proper size. Thirdly, the devices of a circular shape are not the best fit for the adjacent vertebrae being spaced. Fourth, most of the devices have the internal space occupied with mechanisms limiting the amount of bone growth material available for packing the implants.

The wedge type implants generally contact the bone on an angle and expandable wedges when expanded simply expand on an angle not parallel to the vertebrae surface. This places localized high loading between the vertebrae because the wedge surfaces are not parallel to the vertebrae.

In some cases of vertebral misalignment, a controlled angulation of the implant device can be very beneficial to correct a pre-existing condition. Accordingly, in those cases having a wedge shape at a fixed angulation would mean the manufacturer would be required to make many devices with pre-set angles to select from. This simply is cost prohibitive.

Previous ramped methods of expansion limit the range of expansion height, and therefore maximum angle, of the implant by using ramped surfaces directly onto the base plate which contacts the endplate of the vertebral body. Other expansion methods include cylindrical gear drive features, hinged linkages, and cams/ramps forcing base plate(s) apart through plastic deformation of the material. The cylindrical gear drive features limit the amount of bone graft space available within the interbody cage to promote fusion, unsupported hinged linkages reduce load bearing surface area and negatively affect the expansion strength and overall strength of the interbody cage. Other devices use material deformation which limits the amount of expansion capability and reduces the structural integrity of the interbody cage. The present invention overcomes all these deficiencies.

The present invention provides a device that can be expanded angularly to allow the surgeon to choose the ideal lordotic angle he wants to use to correct the spinal alignment.

These and other limitations in the prior art have been corrected and solved by the present invention as disclosed herein.

SUMMARY OF THE INVENTION

An expandable interbody fusion implant device has a frame, two ramp assemblies, a threaded drive shaft and at least one base plate. The frame has a first lateral side and a second lateral side and a distal end and a proximal end. The two ramp assemblies include a distal ramp assembly and a proximal ramp assembly. Each ramp assembly has a translating ramp with a threaded opening, a first pivoting hinged ramp and a second pivoting hinged ramp. The at least one, or optionally two base plates are disposed overlying the frame between the distal end and the proximal end of the frame. Each base plate is hinged to a first lateral side of the frame. A first base plate overlies a second base plate. Each base plate is hinged to the distal ramp assembly and the proximal ramp assembly at an end of one of said pivoting hinged ramps of each ramp assembly. The threaded drive shaft is pinned to the proximal end of the frame. The drive shaft has a distal drive shaft component having threads for translating the distal ramp assembly and a proximal drive shaft component having threads for translating the proximal ramp assembly. Each drive shaft component is coupled to the other. The proximal drive shaft component is affixed to the frame at the proximal end of the frame.

Rotation of the drive shaft drives the distal ramp assembly and proximal ramp assembly simultaneously in opposite directions to selectively expand or contract a distance between the base plate or plates laterally relative the second lateral side of the frame. This simultaneous rotation of both distal and proximal drive shaft components drives the distal and proximal ramps selectively expands or contracts a distance between the first and/or second base plates to a selected inclination of the first or second base plates relative to the frame over a range of lordotic angles.

Each translating ramp has an exterior lift surface to guide and support the pivoting hinged ramps during expansion or contraction of the base plates. During expansion of the base plates the distal ramp assembly moves directionally toward the distal end of the frame on rotation of the distal drive shaft component as the proximal ramp assembly simultaneously moves directionally toward the proximal end of the frame on rotation of the proximal drive shaft component, increasing the inclination of the base plates relative to the frame. This device stops expansion when each translating ramp contacts the distal and proximal wall of the frame. Each pivoting hinged ramp has a bearing support surface configured to slide on the exterior lift surface of the translating ramp. Each pivoting hinged ramp bearing support surface is complimentary to the exterior lift surface, the complimentary surface of each being inclined with a sloped flat feature.

Each translating ramp has a pair of opposing sides, each side has a pair of guide channels or grooves configured to receive a projecting rail positioned inside the frame along each first and second lateral side of the frame. Each base plate has pockets to which the pivoting hinged ramps are pinned and each translating ramp has a hinge guide channel or hinge guide groove for receiving and guiding one of the pivoting hinged ramps. Each pivoting hinged ramp has a lateral side keyed into the hinge guide channel or hinge guide groove.

The distal end of the frame has a tapered end configured to facilitate insertion between vertebral bodies. The proximal end of the frame has an opening for receiving an end of the threaded drive shaft, and further has the first lateral side with slotted channels to receive a hinge pin fixed to the first or second base plates, the hinge pins configured to allow the base plates to pivot relative to the frame during expansion or contraction.

In still another embodiment, the first and optional second base plates each have, at the proximal end, an end plate with a fastener opening for securing the implant to a vertebral body. Each end plate is integral to and movable with the base plate during expansion or contraction. Each end plate further has a locking tab attached to the end plate, the locking tab being rotatable to cover a portion of the fastener from loosening after being affixed to a vertebral body. Preferably, the base plates have a laterally inclined outer surface configured to match or mimic a lordotic curvature of the lumbar spine.

BRIEF DESCRIPTION OF THE DRAWINGS

The invention will be described by way of example and with reference to the accompanying drawings in which.

DETAILED DESCRIPTION OF THE INVENTION

Figure 15A:
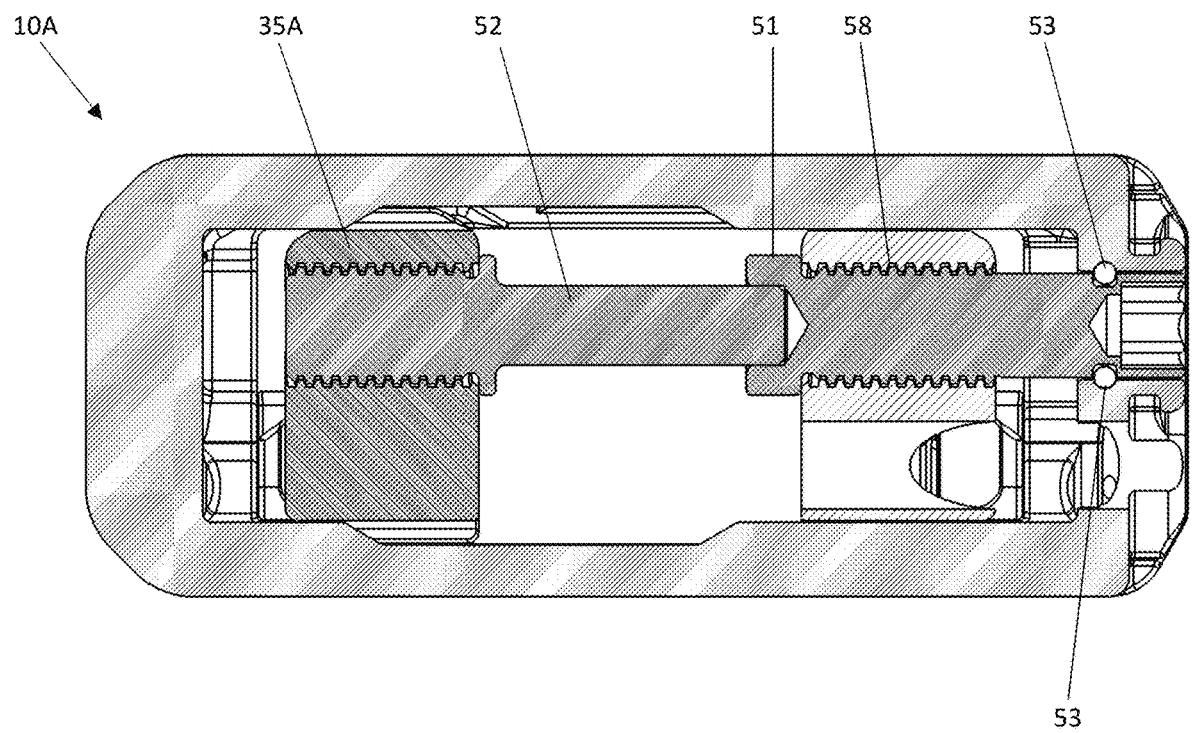
FIG. 15A is a cross-sectional view of the device of the present invention in a contracted position.
Figure 15B:
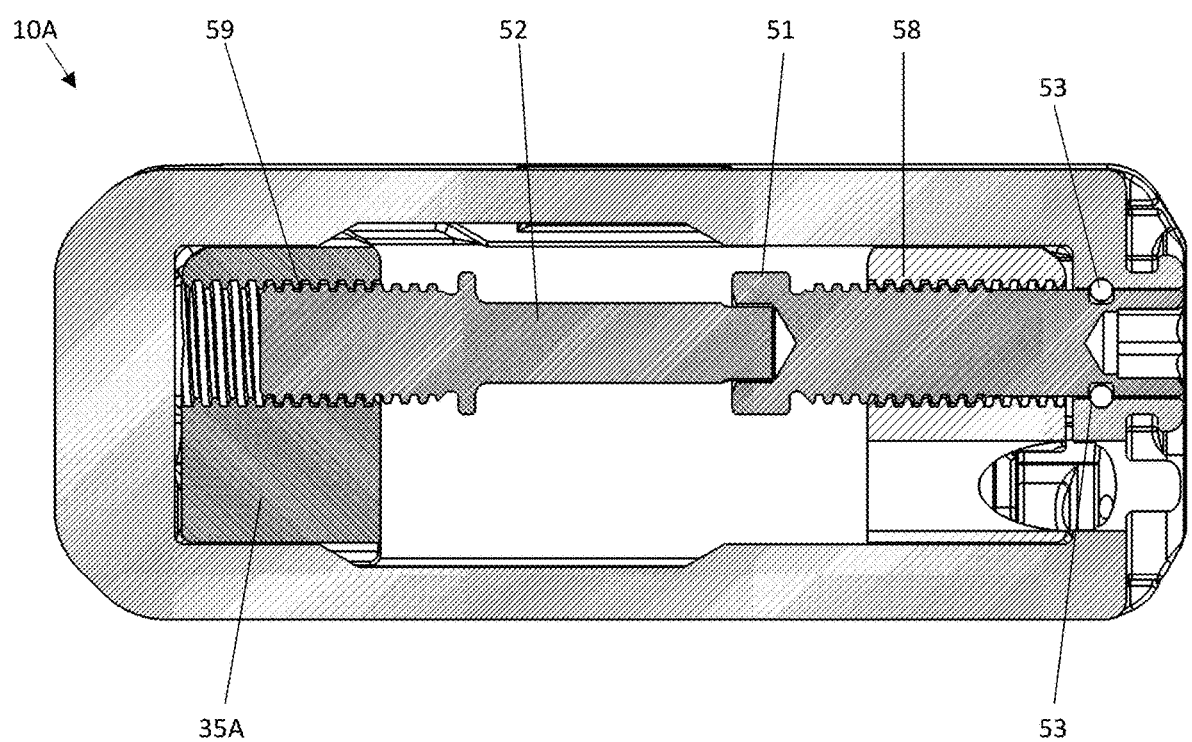
FIG. 15B is a cross-sectional view of the device of the present invention in an expanded position.
Figure 16:
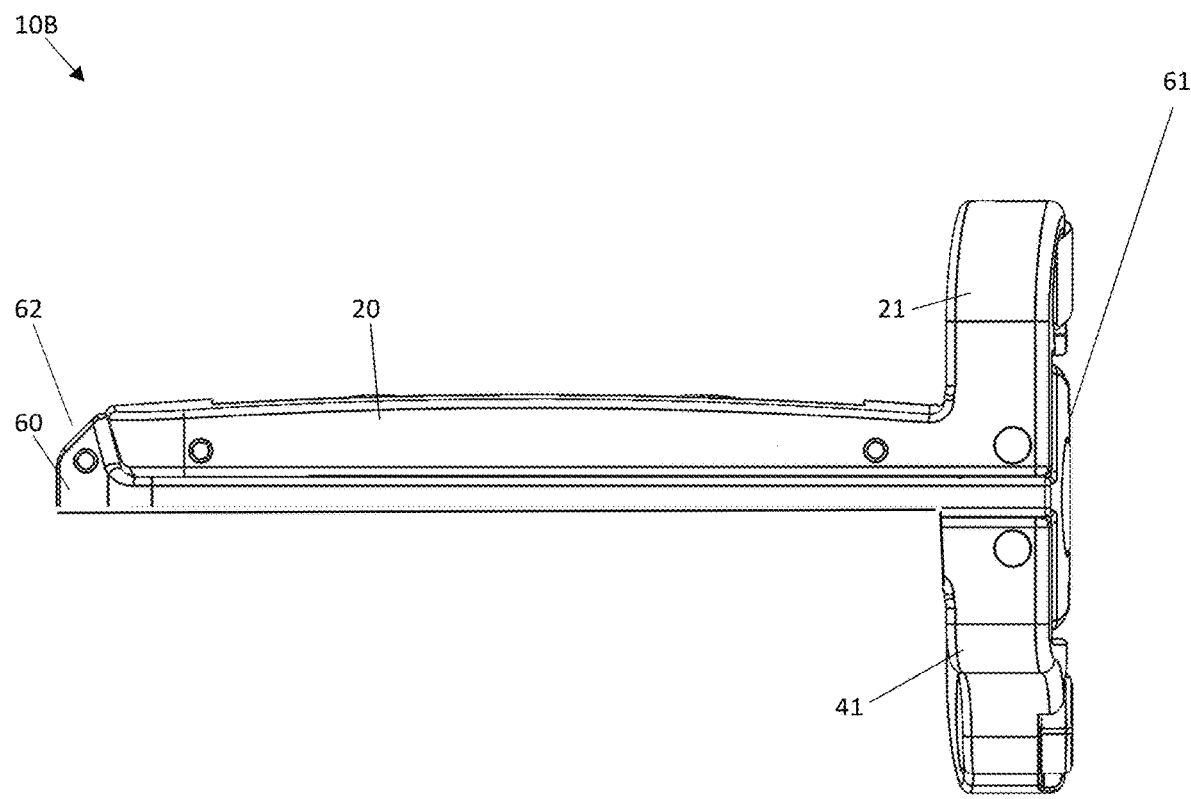
FIG. 16 is a side view of a third embodiment of the invention wherein only a single hinge base plate is shown attached to the frame and the frame has a fixation end plate at the proximal end.

In this present invention, the embodiments exhibit at least one base plate as described herein, the embodiment of FIG. 16 is shown and described employing only one base plate affixed to the frame. All the features of the FIGS. 1-15 exhibiting two base plates and the frame are otherwise the same. The relative movement of the base plate relative to the frame provides the desired lordotic angle. Accordingly, the description of the components and function of the device 10 and 10A are otherwise applicable to the device 10B of FIG. 16 and all of the devices 10, 10A and 10B exhibit at least one base plate.

The purpose of the present invention is to promote spinal fusion with distraction and/or alignment correction of vertebral bodies by implanting the interbody device 10 and expanding the base plates 20, 40 to the appropriate height and angle by controlling fine height adjustment of one side of the implant (anterior side), increasing the lordotic angle. The optional incorporated fixation end plates which expand along with the base plates 20, 40 may be used as in FIG. 1 or may not be used as in FIG. 1A to accept a screw or fastener and lock for fixation of the interbody.

Figure 1:
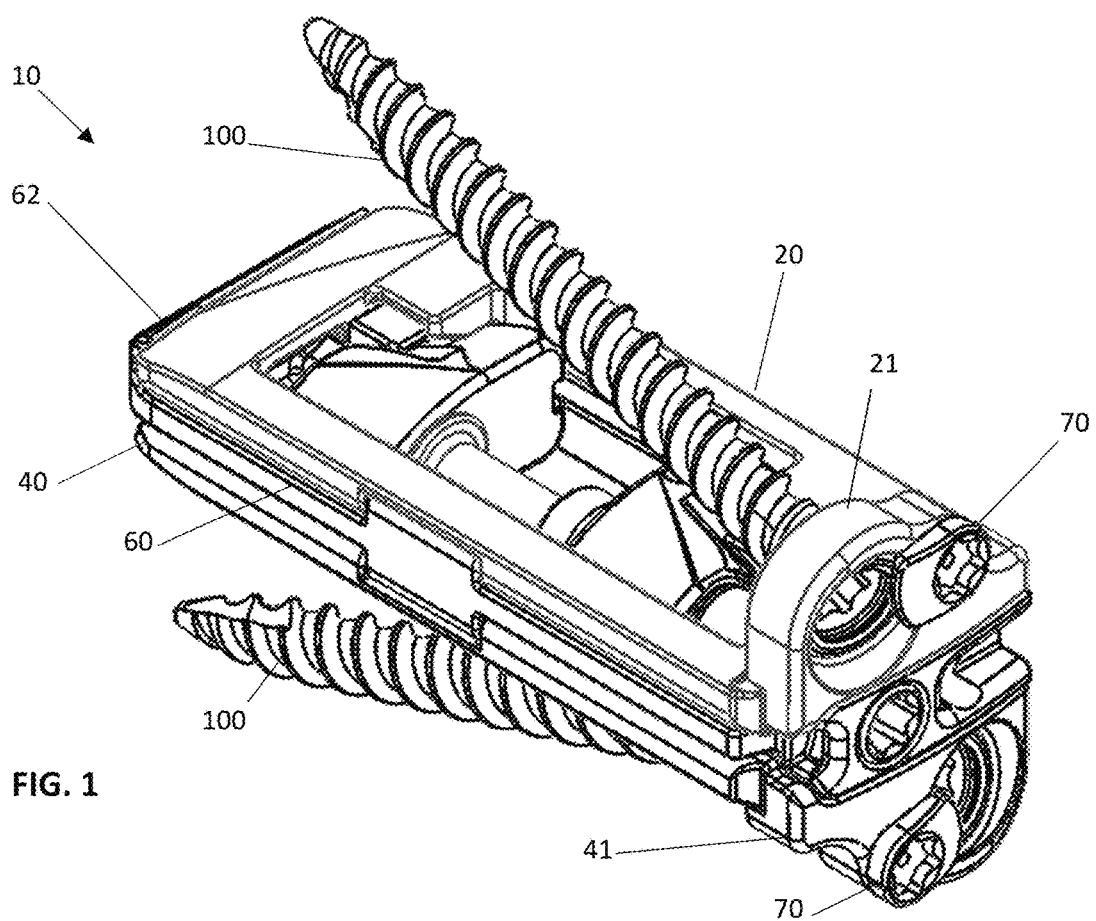
FIG. 1 is a perspective view of the expandable implant device of a preferred embodiment made in accordance with the present invention shown in a contracted non-expanded position.
Figure 1A:
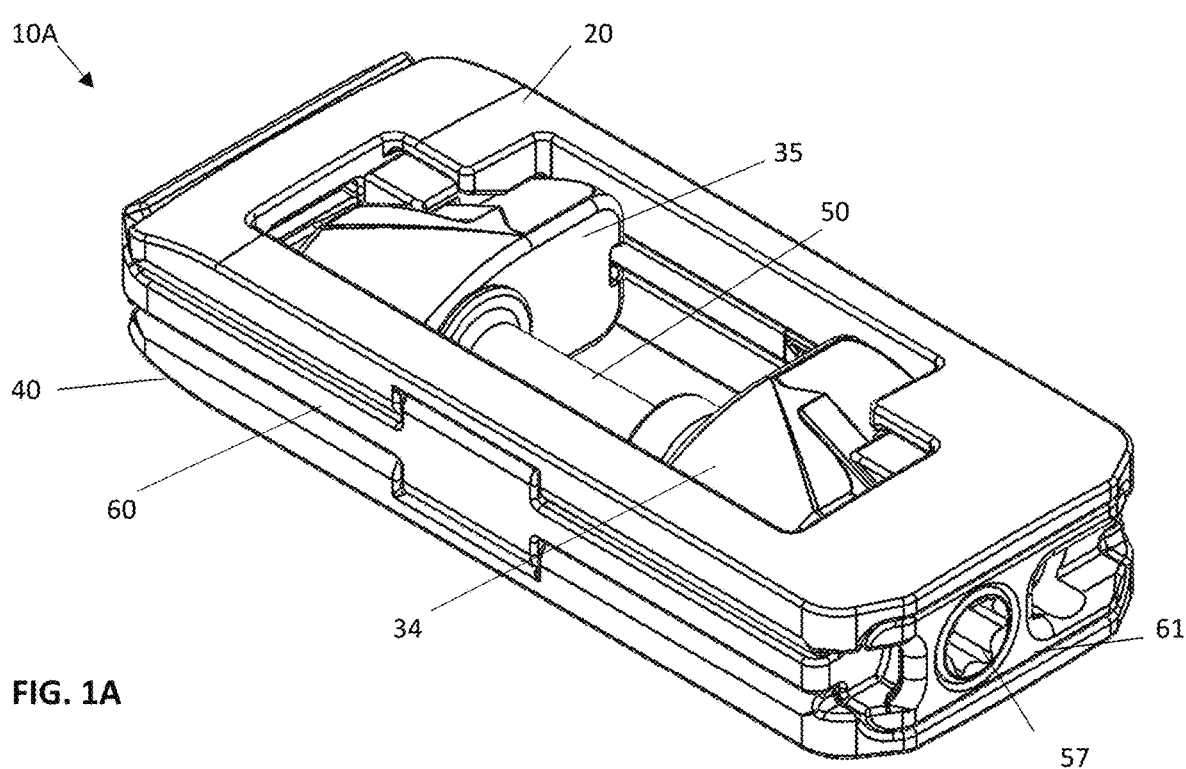
FIG. 1A is an alternative embodiment of the present invention without end plates and fasteners shown in a contracted position.

The intervertebral implant device with lordotic expansion of the present invention, hereinafter described as an expandable interbody fusion implant device 10, has a frame 60, two ramp assemblies, 34A, 35A and two overlying base plates 20, 40 driven by a threaded drive shaft 50 having two coupled drive shaft components 51, 52; as illustrated in FIGS. 1 and 1A. As illustrated in the preferred embodiment of FIG. 1, each base plate 20, 40 has a fixation end plate 21, 41 with an opening 25, 45 for receiving a threaded fastener 100 for attachment to a vertebral body. A locking tab 70 is provided. In FIG. 1A, an alternative embodiment 10A of the device 10 is illustrated without fixation end plates 21, 41 or threaded fasteners 100. In all other respects the devices 10, 10A are the same.

Figure 2:
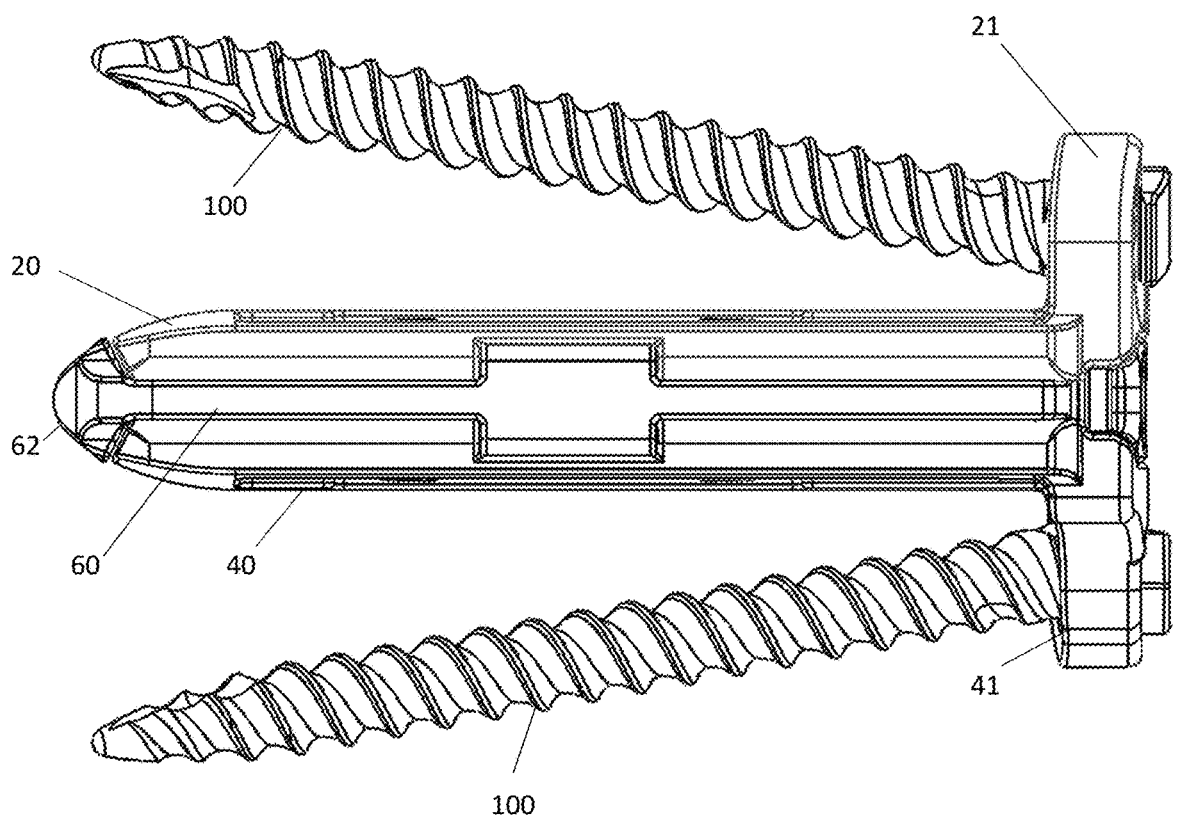
FIG. 2 is a side view of the expandable implant device taken from FIG. 1.

With reference to FIGS. 1 and 2, the device 10, 10A shows the frame 60 having a distal end 62 and a proximal end 61. The two ramp assemblies 34A, 35A include a distal translating ramp 35 and a proximal translating ramp 34 respectively, and further have a first pivoting hinged ramp 31 and a second pivoting hinged ramp 33 held by pins 85 in pockets or recesses in each base plate 20, 40. The two overlying base plates 20, 40 are disposed between the distal end 62 and the proximal end 61. The first base plate 20 overlies the second base plate 40 with the frame 60 interposed between. Each base plate 20, 40 is hinged to a distal ramp assembly 35A and the proximal ramp assembly 34A at an end of one of the said pivoting hinged ramps 31, 33 of each ramp assembly 34A, 35A by the pivoting hinged ramps held by pins 85 in the pockets or recesses of each base plate and further hinged with pins 82 along a first lateral side of the frame 60. Each base plate 20, 40 being pivotally moveable about the hinge of the frame 60. The drive shaft 50 include a distal drive shaft component 52 for translating the distal ramp assembly 35A and a proximal drive shaft component 51 for translating the proximal ramp assembly 34A. The drive shaft 50 is affixed to the frame 60 at the proximal end with pins 53.

As shown in FIGS. 1 and 2, the implant device 10 is shown in a fully contracted position, this position is most suitable for insertion as it provides the lowest height between the opposing base plates 20, 40. As shown, the distal end 62 has a chamfered leading end surface further reducing the cross section as it enters between the intervertebral spaces providing a nice leading nose end for insertion. At the proximal end of the implant device 10, each base plate 20, 40 respectively has fixation end plates 21 and 41. These fixation end plates 21, 41 each are provided with a through hole 25 for receiving a threaded fastener 100.

Figure 3A:
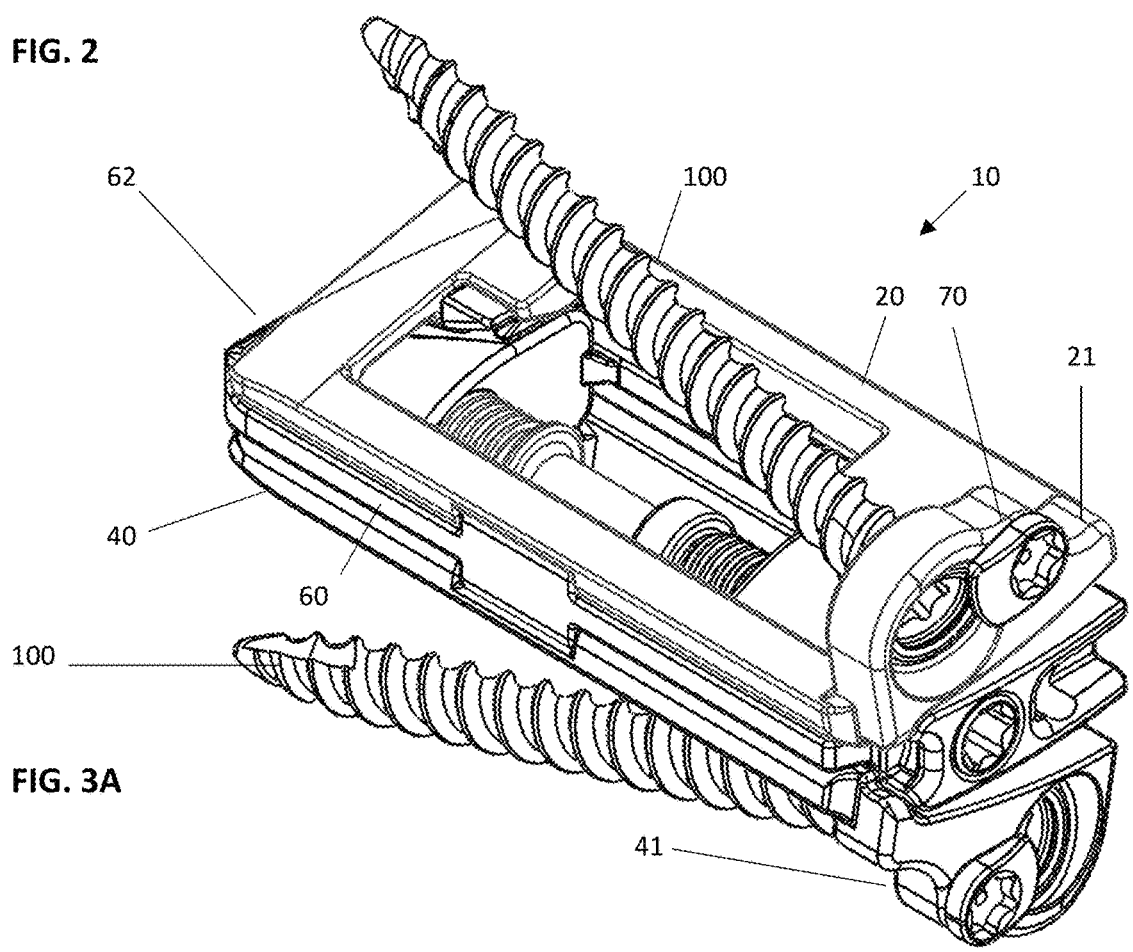
FIG. 3A is a perspective view of the device of FIG. 1 shown expanded.
Figure 3B:
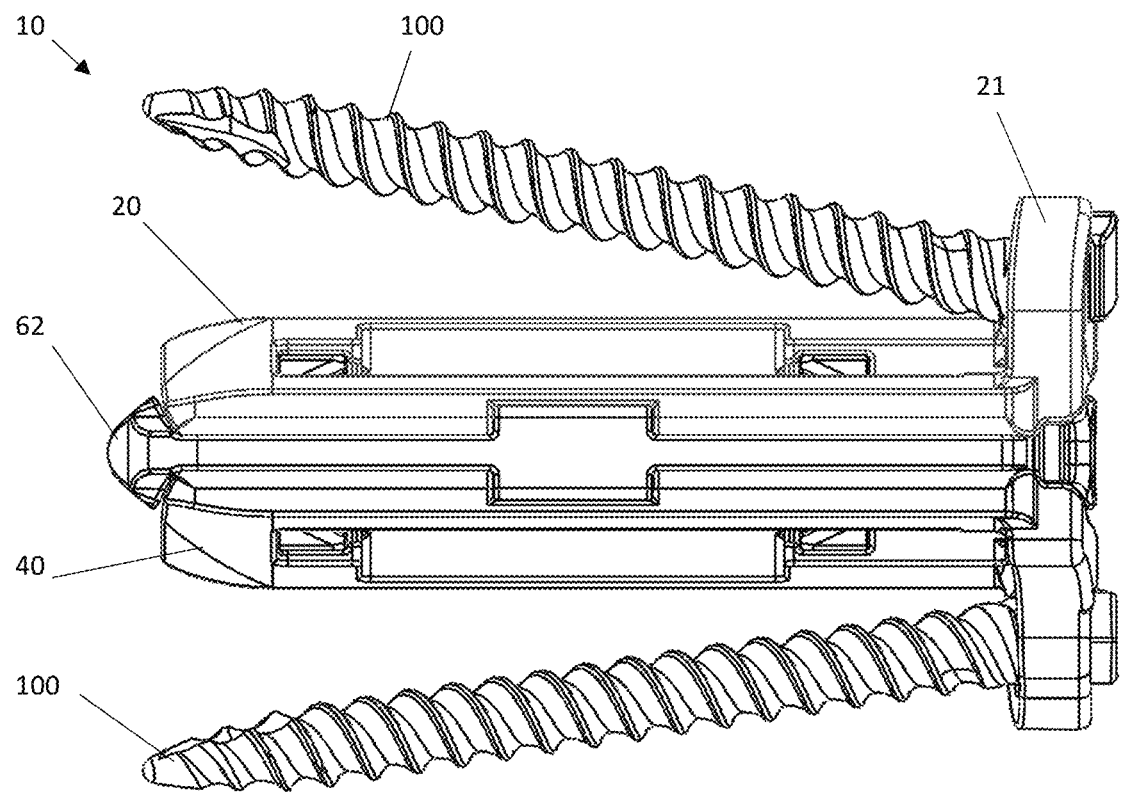
FIG. 3B is the side view taken from FIG. 3A with threaded fasteners installed in the proximal end of each first and second base plate.

With reference to FIGS. 3A and 3B, the implant device 10 is shown where the threaded drive shaft 50 has been rotated, the distal drive shaft component 52 has threads 59 engage threads 95 in the translating ramp 35 that cause the distal ramp assembly 35A to be moved towards the distal end of the frame 62. When this occurs, the translating ramp 35 of the distal ramp assembly 35A moves the pivoting hinged ramps 31 and 33 along an outer surface of the translating ramp 35 following the contour of the outer surface. Simultaneously, when this drive shaft 50 is rotationally driven it rotates the proximal drive shaft component 51 causing the base plates 20, 40 both to be expanded increased in height from the contracted state to an expanded state as the base plates 20, 40 pivot. The drive shaft 50 is assembled from two components 51, 52 and the proximal component 51 is pinned with pins 53 into the frame 60 at the proximal end of the interbody to maintain positioning and prevent translation. The drive shaft 50 threads into both the distal translating/expanding ramp 35 and the proximal translating/expanding ramp 34 to drive both ramp assemblies simultaneously. To accomplish this movement, the distal drive shaft component 52 has threads 59 opposite to the proximal drive shaft component 51 threads 58, one thread being left handed the other thread right handed.

Figure 4A:
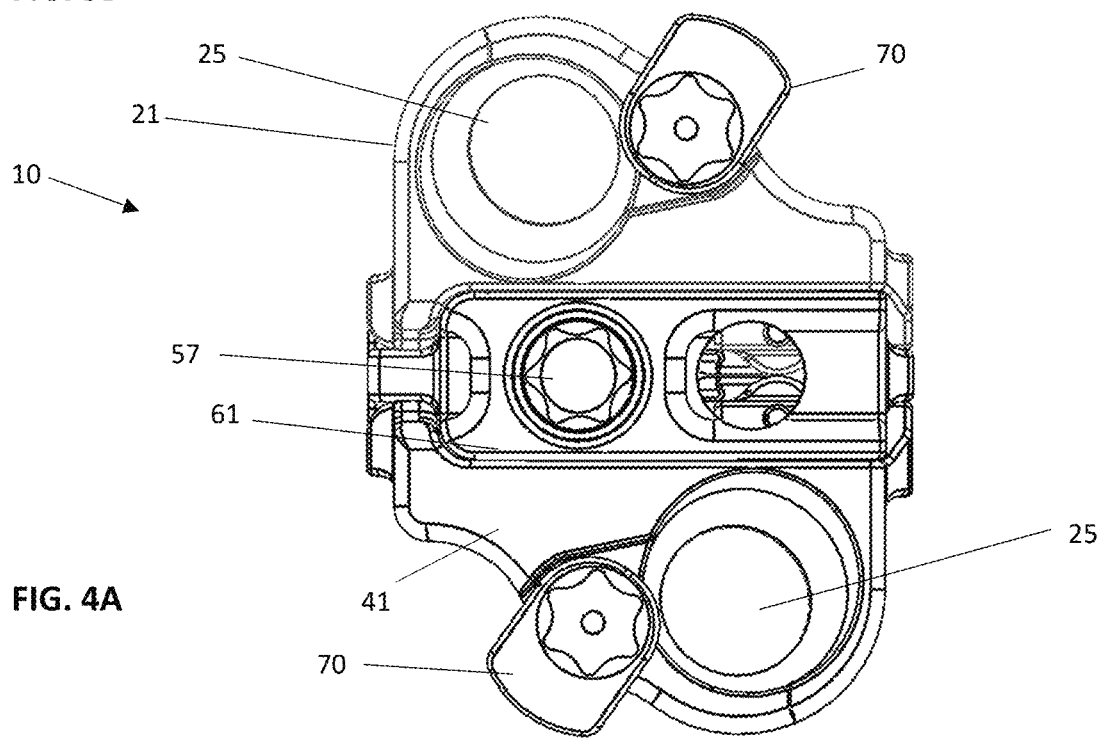
FIG. 4A is a proximal end view of the device of FIG. 1 shown contracted without fasteners.
Figure 4B:
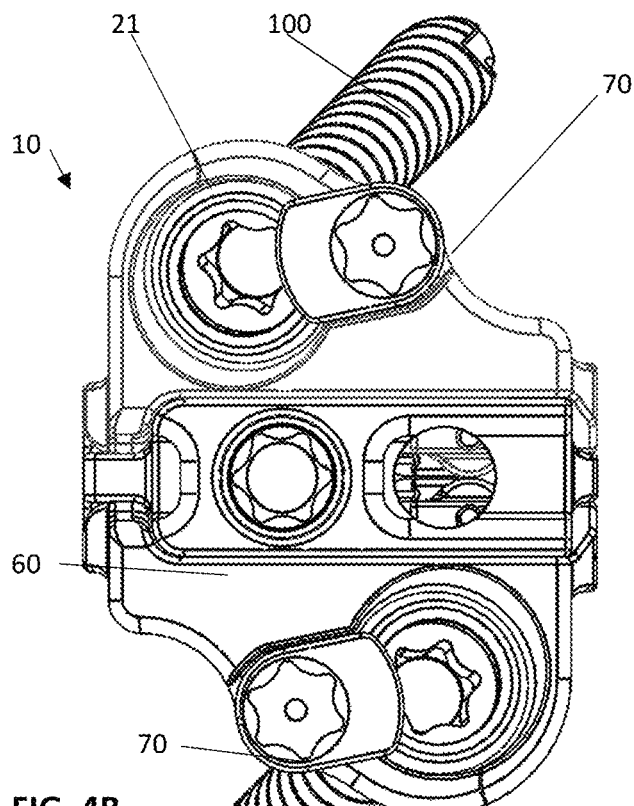
FIG. 4B is a proximal end view taken from FIG. 4A with fasteners.
Figure 4C:
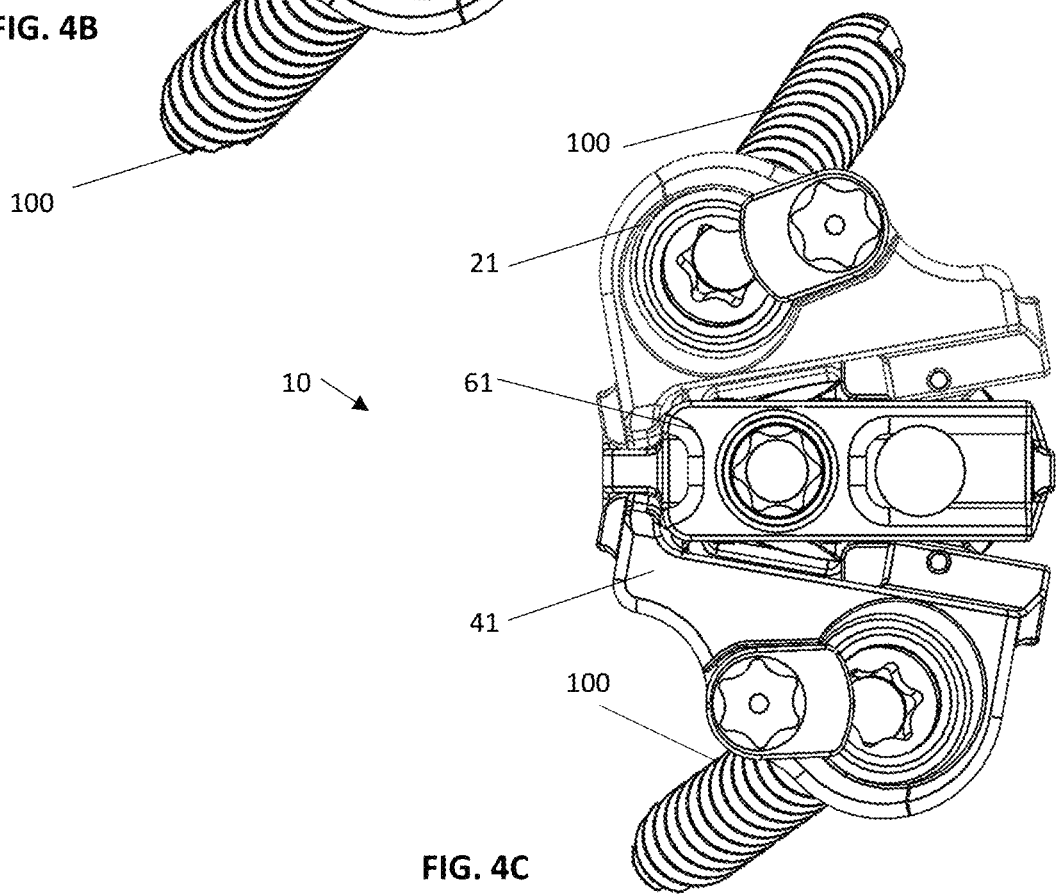
FIG. 4C is a proximal end view taken from FIG. 4B with threaded fasteners installed in the proximal end of each first and second base plate with the device shown expanded.

This increase in height can occur in small increments anywhere dependent on the amount of the rotation of the drive shaft 50 and this rotation achieves a maximum level when the translating ramp 34, 35 contacts the distal or proximal wall of the frame 60. In the fully expanded condition, the lateral side of each base plate is shown elevated relative to the frame. This can best be seen in FIG. 3B from a side view or 4C from a front view. Threaded fasteners 100 can be inserted through the through holes 25 in both the first fixation end plate 21 and the second fixation end plate 41 of the first base plate 20 and the second base plate 40 respectively at any selected angle or expansion. FIG. 4A best shows the through holes 25 without the fasteners 100. FIGS. 4B and 4C show the end view of the device 10 in the contracted and fully expanded positions.

Figure 5A:
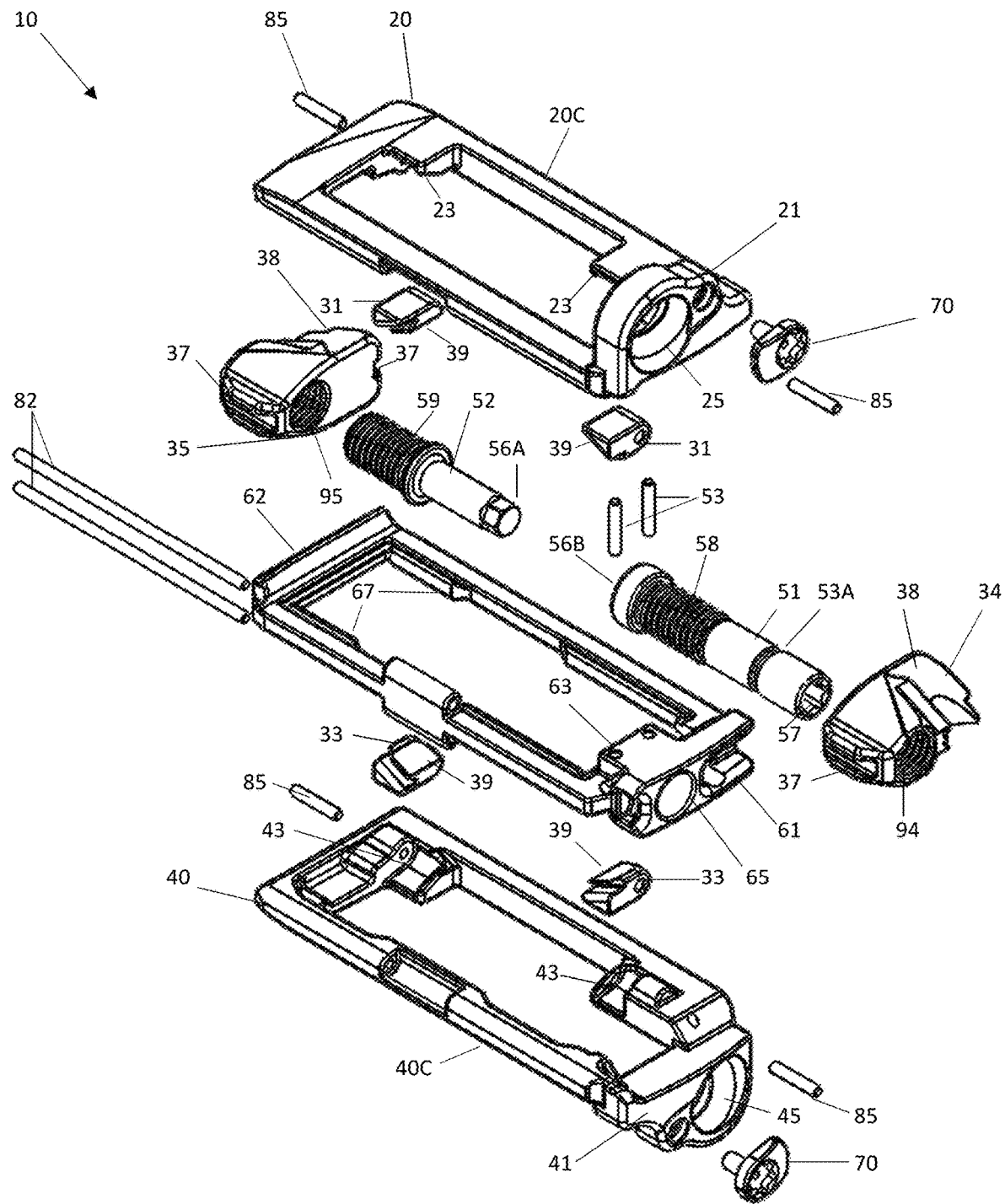
FIG. 5A is a perspective exploded view of the device of FIG. 1 shown without the fasteners.
Figure 5B:
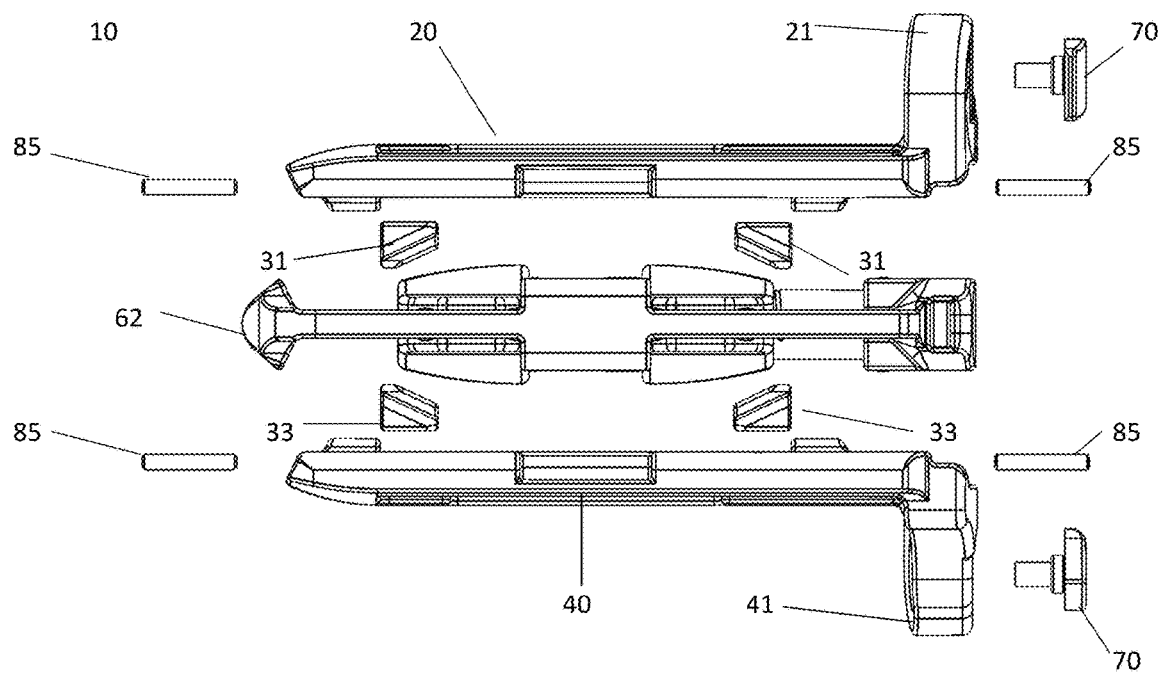
FIG. 5B is a side view of the device taken from FIG. 5A showing the frame and the drive shaft and translating ramp assemblies assembled.
Figure 5C:
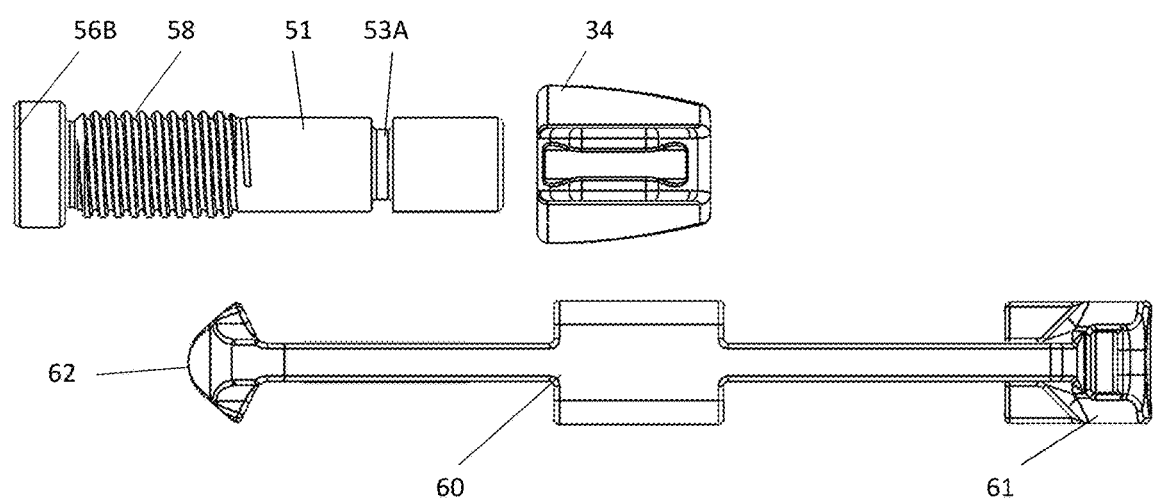
FIG. 5C is a side view taken of the proximal end of the drive shaft and proximal translating ramp and the frame.

With reference to FIGS. 5A-5D, various exploded views of the components of the implant device 10 are shown. With reference to FIGS. 5A, 5B the ramp assemblies 34A, 35A are shown as individual components, the translating ramps 34, 35 and the pivoting hinged ramps 31, 33 respectively are illustrated. As shown the translating ramps 34, 35 have an outer contour 38 on both an upper and a lower surface of each translating ramp 34, 35 and have a dovetail key or projection 37 on each ramp 34, 35. This key 37 allows lateral sides of the pivoting hinged ramps 31 and 33 with a grooved keyway to enter in a dovetail configuration and lock into the translating ramps 34, 35 while maintaining an ability to slide relative to the other. The inner bearing surface 39 of both the pivoting hinged ramps 31, 33 ride on the outer lift surface 38 of the translating ramps 34 and 35 respectively. In this fashion, during the elevation of the implant 10 from contracted to expanded, the pivoting hinged ramps 31, 33 rest securely on the lift surface 38 on both lateral sides of the translating ramp 34, 35 and the base plates 20, 40 hinged to the pivoting hinged ramps 31, 33 at both lateral ends are fully supported across the lateral width of the implant device 10 as the pivoting hinged ramps 31, 33 press against the respective pockets of each base plate. In this construction, there are no gaps between the base plates 20 and 40 as the lift surfaces 38 of the translating ramps 34, 35 and bearing surfaces 39 of the pivoting hinged ramps 31, 33 as well as upon expansion the hinged ramps contact the pockets of the bases 20, 40 as shown best shown in FIG. 8D. All load supporting elements are moved into contact during expansion. Accordingly, the device 10, 10A is extremely rigid between the vertebral bodies and capable of supporting large loads without deflection or deformation when expanded. The hinged lateral side of the base plates 20, 40 being fully supported by the frame 60 and the expanding lateral side are both fully supported. With reference to FIG. 5C, the frame 60, shown slightly below the proximal translation ramp 34 and the proximal drive shaft component 51, the frame 60 is a singular piece having a distal end 62 that has a tapered exterior surface to facilitate insertion.

The fixation end plates 21, 41 accept a locking tab 70 used to lock the bone screws 100 to the fixation end plates 21, 41. The base plates 20, 40 are pinned with pins 85 to all four pivoting hinged ramps 31, 33 at the hinged points to maintain a bearing surface between the pivoting hinged ramps 31, 33 and base plates 20, 40 as well as between the pivoting hinged ramps 31, 33 and translating ramps 34, 35 at all interbody states. The base plates 20, 40 are also assembled to the frame 60 with a hinge pin 82 for each top and bottom base plates 20, 40 as shown. The base plates 20, 40 feature a contoured surface 20C, 40C to match the surface of the vertebral body endplates. The tangent planes of the base plates' 20, 40 contoured surfaces can be either parallel or intersecting. A bone screw or threaded fastener 100 can be inserted into each fixation end plates 21, 41 through the screw holes 25, 45 located on the integrated fixation end plates 21, 41 as shown. The alternative embodiment device 10A does not include an integrated fixation plate, as shown in FIG. 1A.

Each translating ramp 34, 35 has a groove 37 on each side that slides over the rails 67 on each lateral interior side of the frame 60, as shown with a gap between the rails 67 is provided to allow the assembly to the frame 60. These features increase the support and rigidity of the device at all positions of expansion. The base plates 20, 40 also have depressions or pockets into which the pivoting hinged ramps 31, 33 fit and are pinned by the pins 85.

Figure 5D:
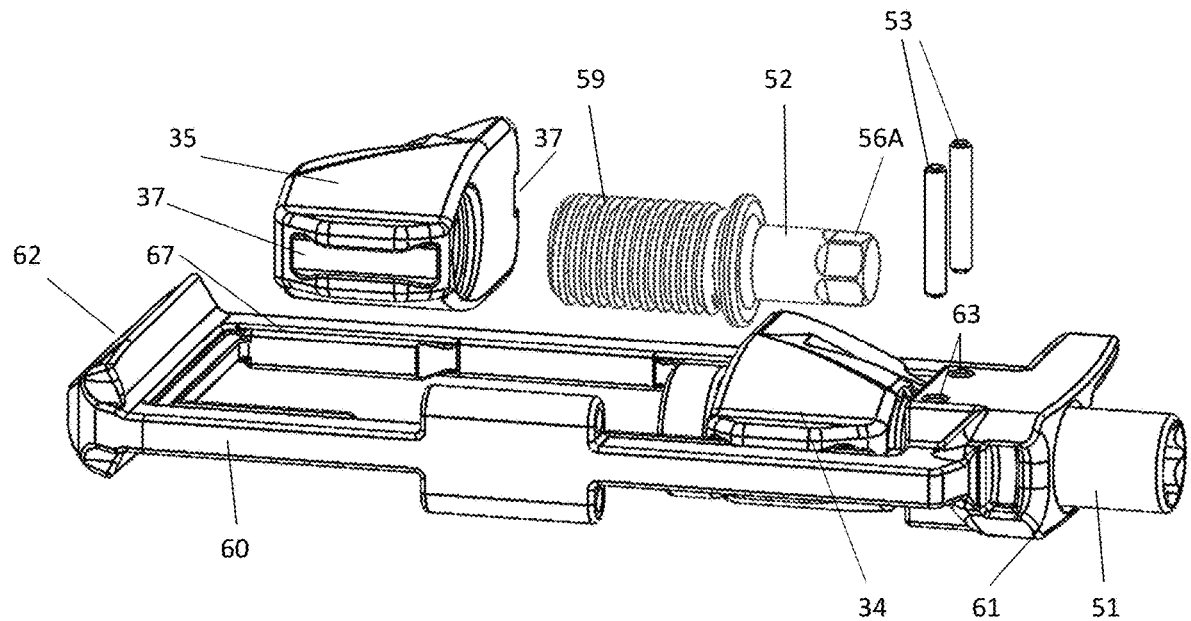
FIG. 5D is an exploded perspective view of the device of FIG. 5A with the proximal portion of the drive shaft prior installed in the proximal end of the frame and the pins not yet installed and the distal drive shaft component and distal ramp shown above the frame.

With reference to FIG. 5D, the frame 60 is shown with the proximal drive shaft component 51 positioned into the proximal end of the frame 60 with the proximal translation ramp 34 threaded onto the proximal drive shaft component 51. Shown above the frame 60 are a pair of pins 53 that are used to secure the proximal drive shaft component 51 in grooves 53A to the frame 60. Also shown above the frame 60 is the distal drive shaft component 52 with threads 59. The distal drive shaft component 52 has a hexagonal head 56A. The distal translating ramp 35 is shown adjacent the distal drive shaft component 52. The distal translating ramp 35 is shown with each lateral side having a groove 37. These grooves 37 fit onto rails 67 on the interior walls of the frame 60.

Figure 6A:
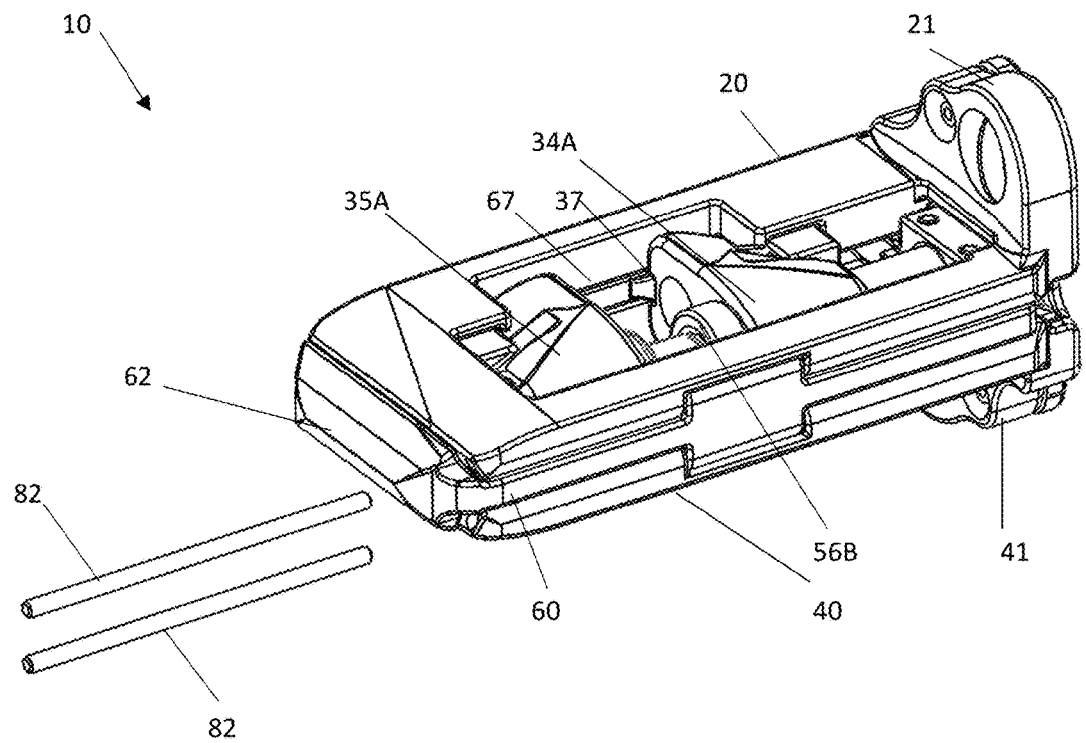
FIG. 6A is an exploded side view of the device of the present invention as a final assembly step showing hinge pins for securing the base plates to the frame.

With reference to FIG. 6A, the distal drive shaft component 52 is shown connected to the female 12-point socket 56B of the proximal drive shaft component 51 coupling the two drive shaft components 51, 52 together to form the drive shaft 50. The base plates 20, 40 are shown with openings to receive hinge pins 82, each hinge pin 82 connects a base plate 20, 40 to the frame 60 allowing the base plates 20, 40 to pivotally move relative to the frame 60 secured by the hinge pins 82.

Figure 7A:
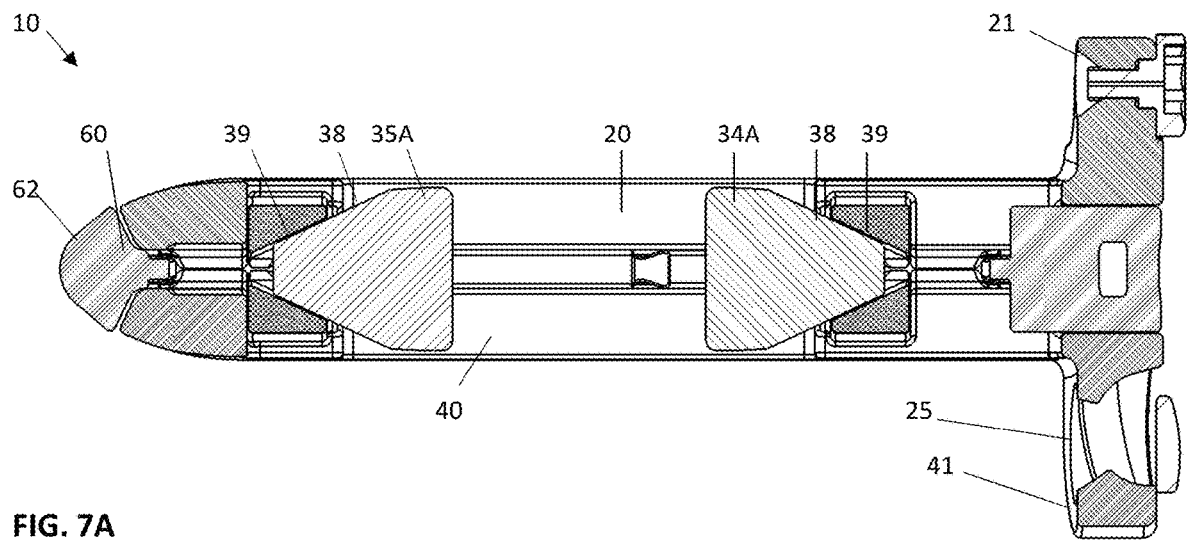
FIG. 7A is a side cross-sectional view of the device of the present invention with the drive shaft rotated to a fully contracted position.
Figure 7B:
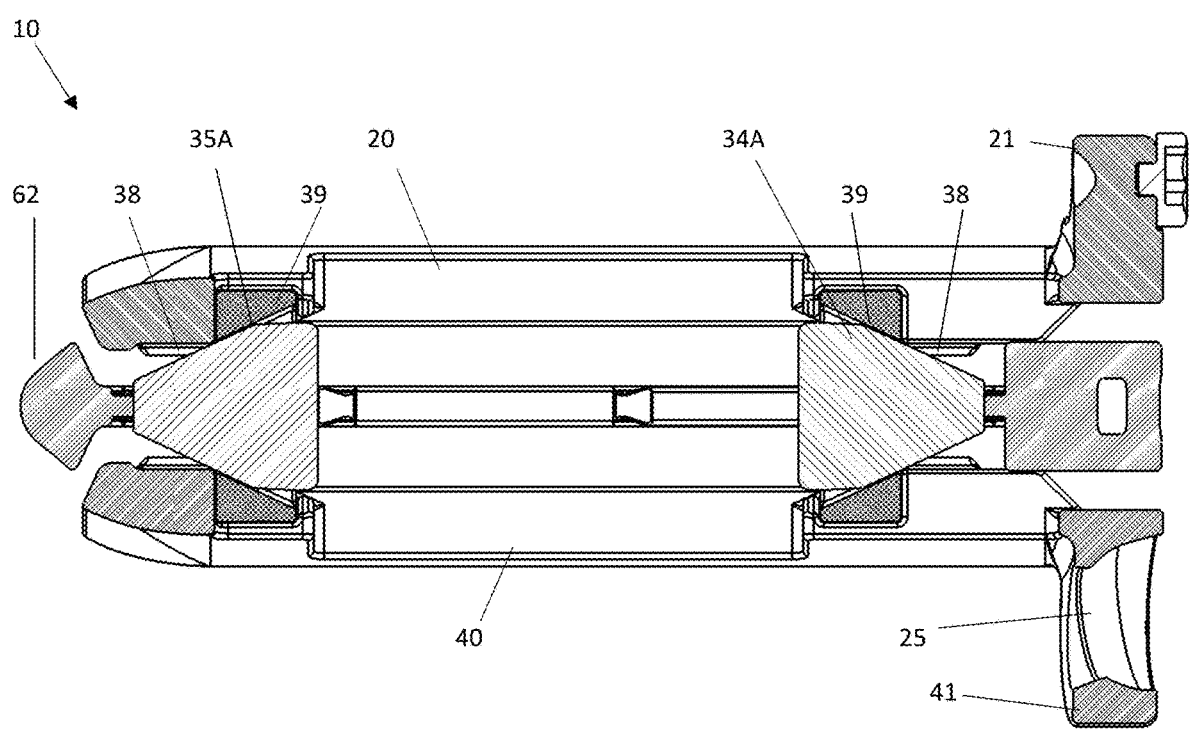
FIG. 7B is a side cross-sectional view of the device of the present invention with the drive shaft expanded.

With reference to FIGS. 7A and 7B, cross sectional views of the device 10 are shown. In FIG. 7A, the device 10 is shown in the contracted position with the translating ramps 34, 35 positioned closer to the midline or center of the device or frame 60. In this position, the pivoting hinged ramps 31, 33 are positioned on the lower or contracted positon and therefore are shown hanging down and bearing against the lift surfaces 38 of the translating ramps 34, 35 respectively. With reference to FIG. 7B, as the drive shaft 50 is rotated, the translating ramps 34, 35 move outwardly toward the proximal and distal ends, respectively. As this occurs, the bearing or support surface 38 is increasing in height forcing the pivoting hinged ramps 31, 33 to elevate as they ride along this surface 38 tending to push the base plates 20, 40 pivotally about the pivot or hinge pin 82 and increasing the distance between the base plates 20, 40. When this occurs, the distal end 62 is shown exposed with the plates shown extended above that end of the device 10, 10A.

Figure 8A:
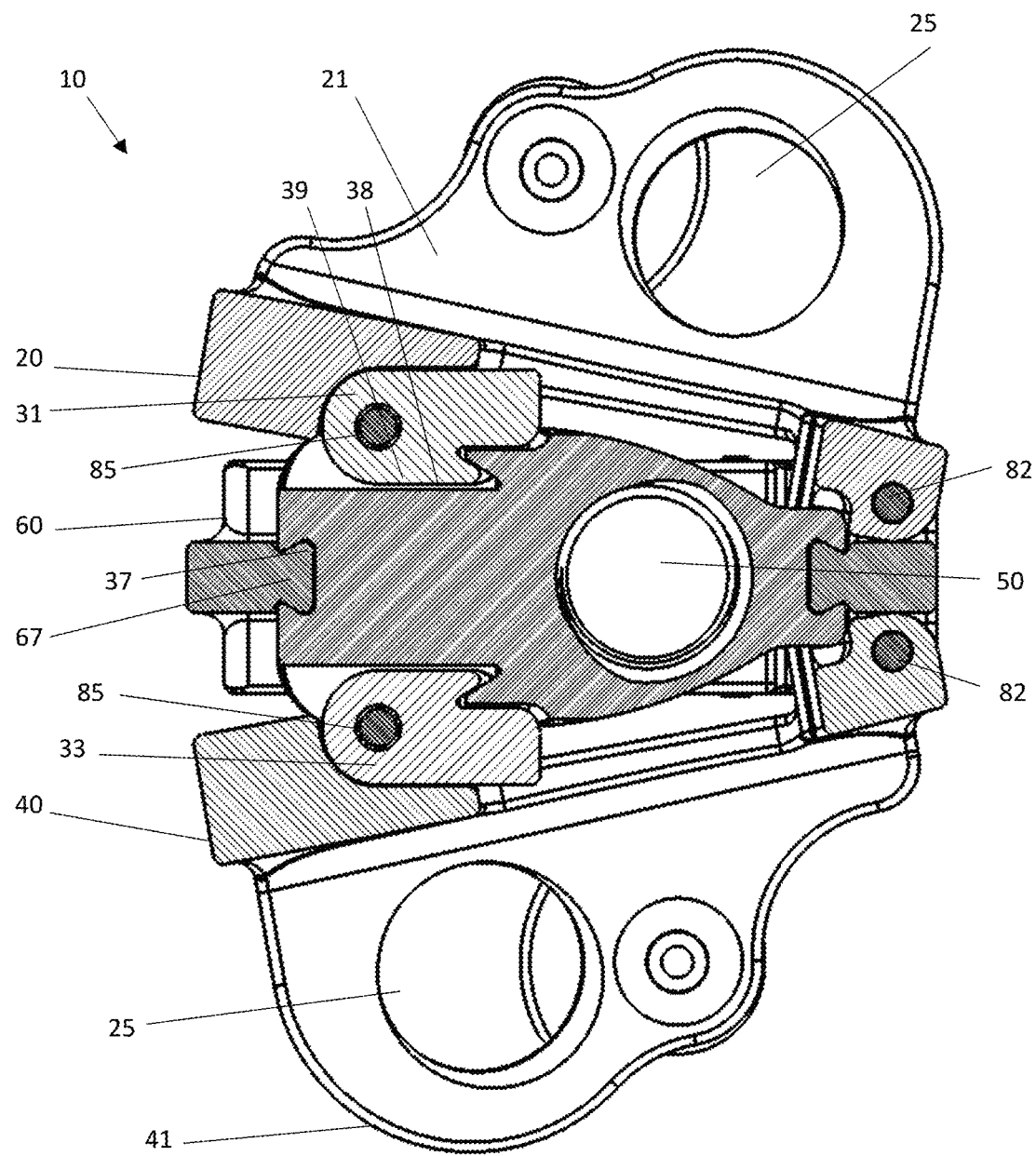
FIG. 8A is an end cross-sectional view of the device of the present invention with the ramp assembly shown with drive shaft expanded.

With reference to FIG. 8A, an end view of the device is illustrated in the fully expanded position. As shown, the translating ramp 34, 35 is shown positioned over the drive shaft 50 in an extended positon. When this occurs, the base plates 20, 40 pivot about the hinge pins 82 securely fixed to the frame 60. The side opposite the hinge pins 82 has an increased expanded height between the base plates 20, 40 relative to the frame 60. When this occurs, the pivoting hinged ramps 31, 33 are shown almost horizontal abutting the pocket of the base plates 20, 40. Hinge 31 shown in the upper position, 33 in a lower position pinned by pins 85 to the base plates. As shown, the pivoting hinged ramps 31, 33 are dovetailed and keyed onto the translating ramps 34, 35 in this elevated position and during expansion, the translating ramps 34, 35 slide along the dovetail as the pivoting hinged ramps 31, 33 elevate increasing the expansion height of the device 10.

Figure 9A:
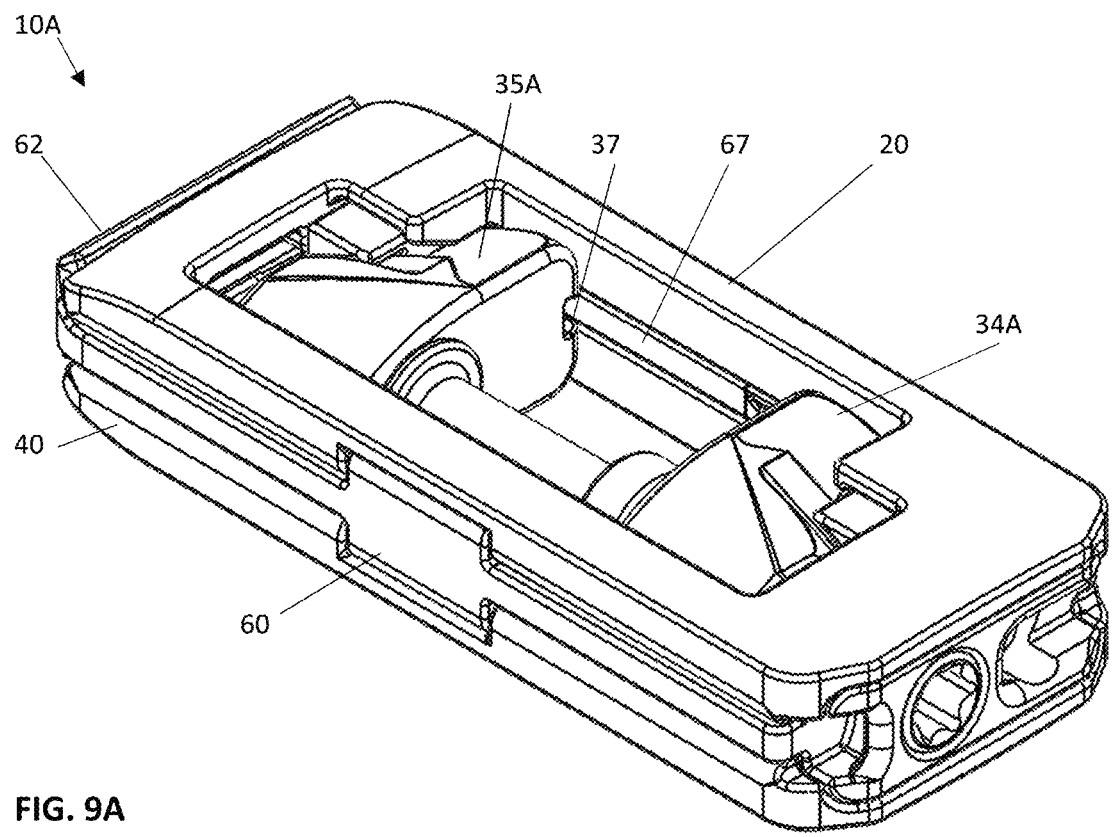
FIGS. 9A, 9B and 9C are isometric views of the alternative embodiment device with no end plates shown contracted partially expanded and fully expanded.
Figure 9B:
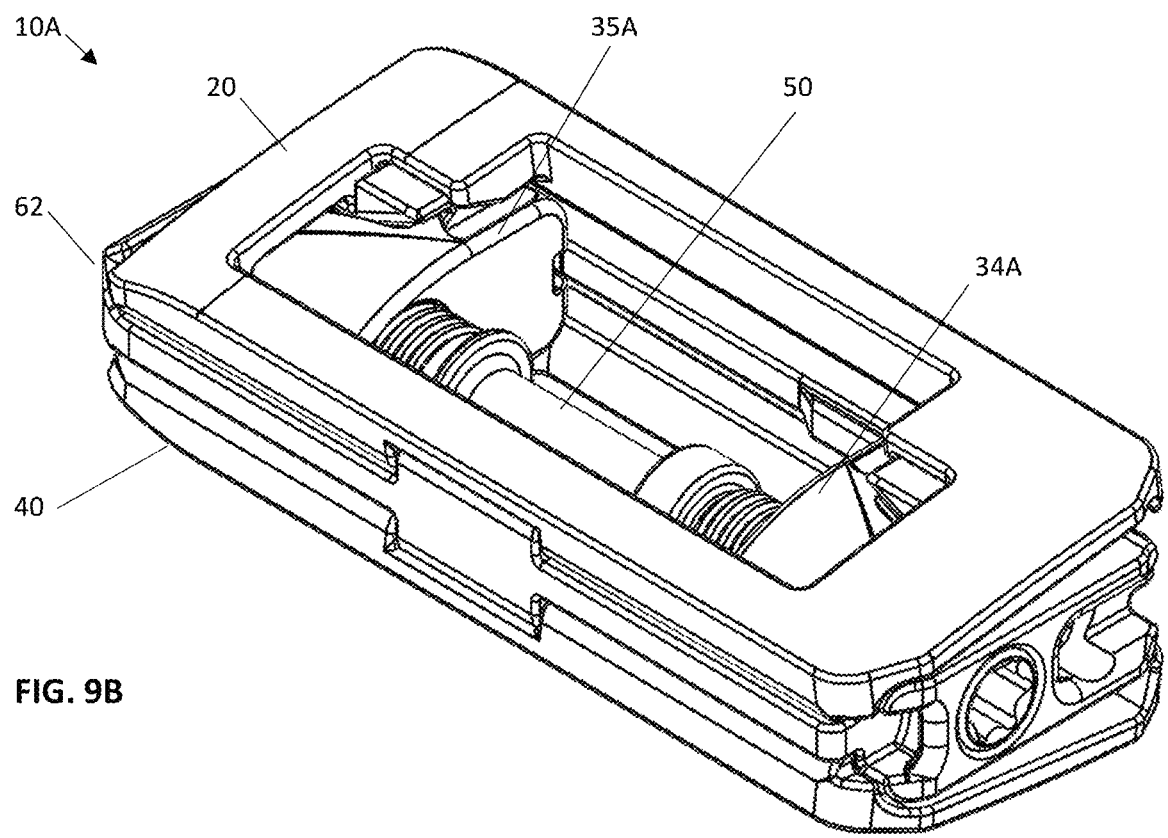
Figure 9C:
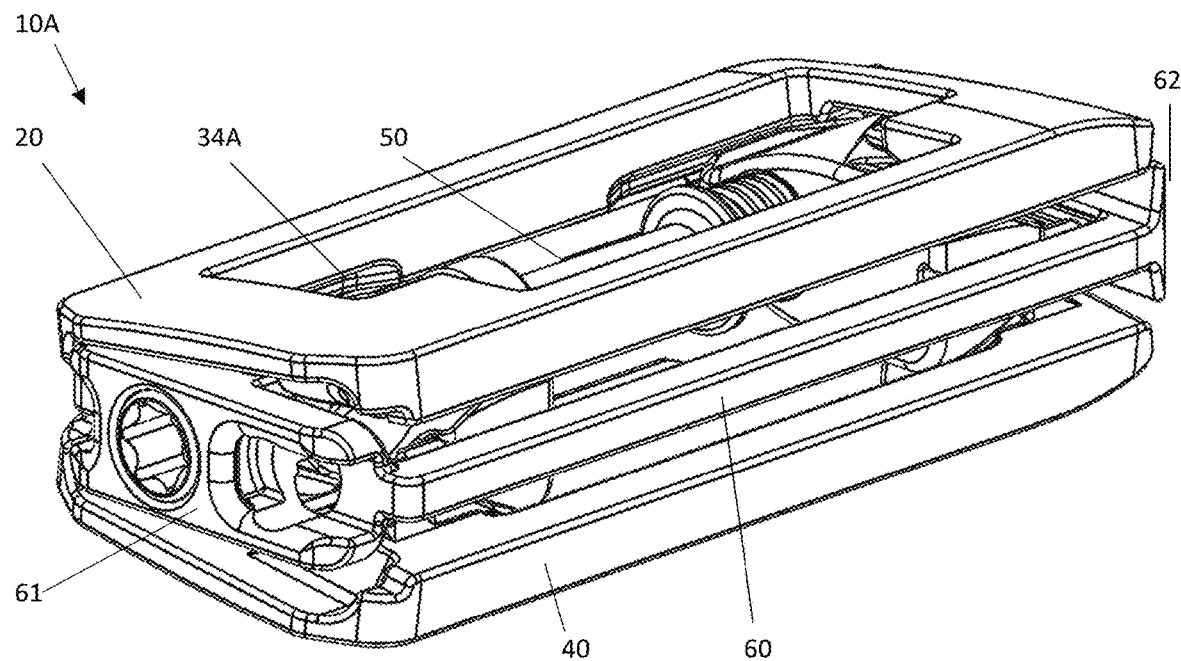

With reference to FIGS. 9A and 9B, the alternative device 10A without fixation end plates is illustrated. In FIG. 9A, the device 10A is shown in the contracted position. In FIG. 9B, the device 10A is shown in the expanded position. All the elemental components are otherwise the same as in the device 10 previously discussed. As shown in FIG. 9A, the translating ramps 34, 35 slide along the rail 67 of the frame 60 by use of a groove 37 on each side of the translating ramps 34, 35. When the device 10A is in the contracted position, the translating ramps 34, 35 are moved towards the center of the device 10A and the threads 58, 59 of the drive shaft are basically covered by the translating ramps 34, 35. When the device 10A is in the expanded position, as shown in FIG. 9B the threads 58, 59 are exposed showing the translating ramps 34, 35 have moved outwardly, the distal translating ramp 35 towards the distal end and the proximal translating ramp 34 towards the proximal end of the device 10A. When this occurs, the device 10A is in the elevated position. The surgeon can select any position from fully contracted to fully expanded or anywhere in between to choose the desired angle and increase in elevation of the device 10A as it is expanded. FIG. 9C best illustrates how the base plates 20, 40 on the side of the device 10A opposite the hinged side expand away from the frame 60 in the expanded position.

Figure 10A:
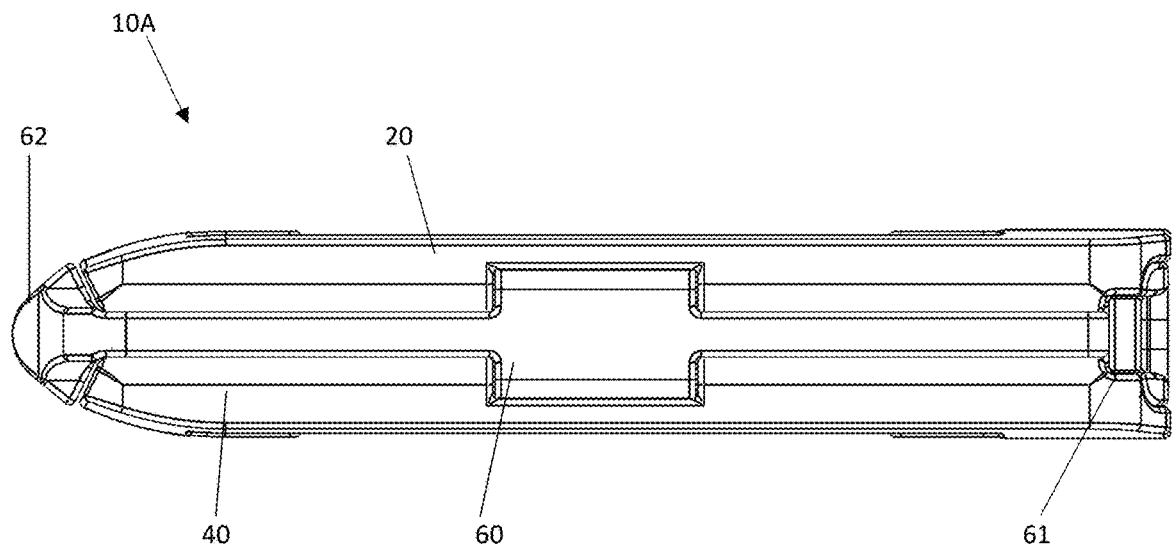
FIGS. 10A and 10B are side views of the device of 1A shown contracted and fully expanded, respectively.
Figure 10B:
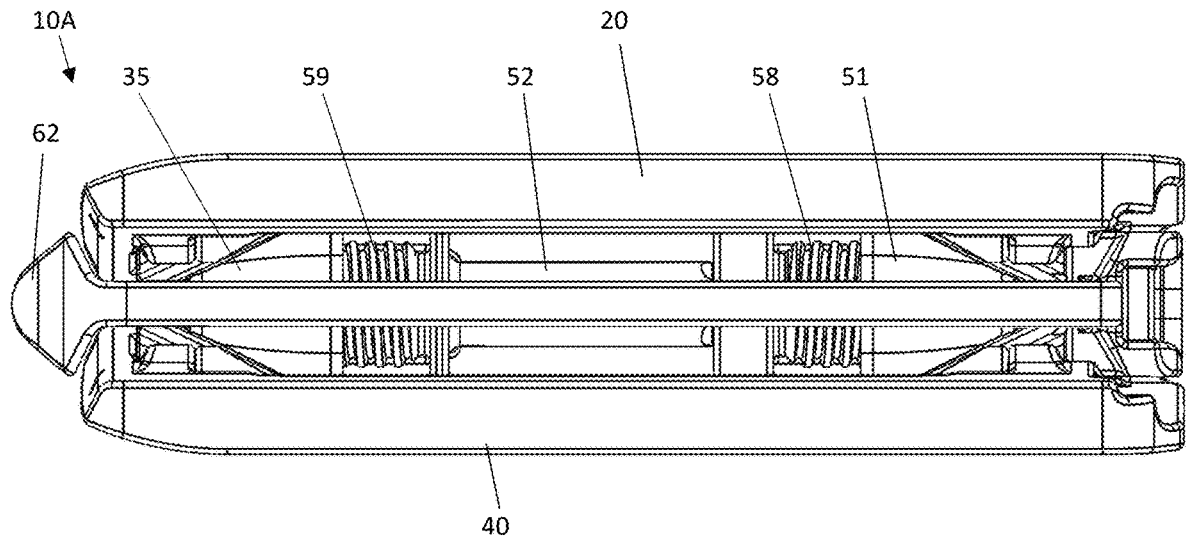

With reference to FIG. 10A, a side view of the device 10A is illustrated in the contracted position. With reference to FIG. 10B, the same device 10A is shown in the expanded position.

Figure 11A:
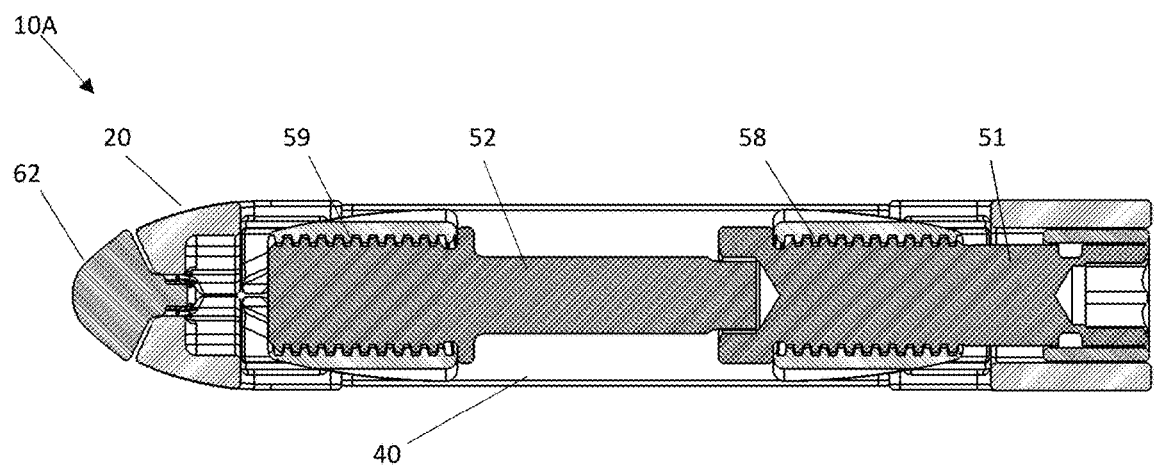
FIGS. 11A and 11B are cross sectional views of the device of FIG. 1A taken from FIGS. 10A and 10B, 11A from 10A and 11B from 10B.
Figure 11B:
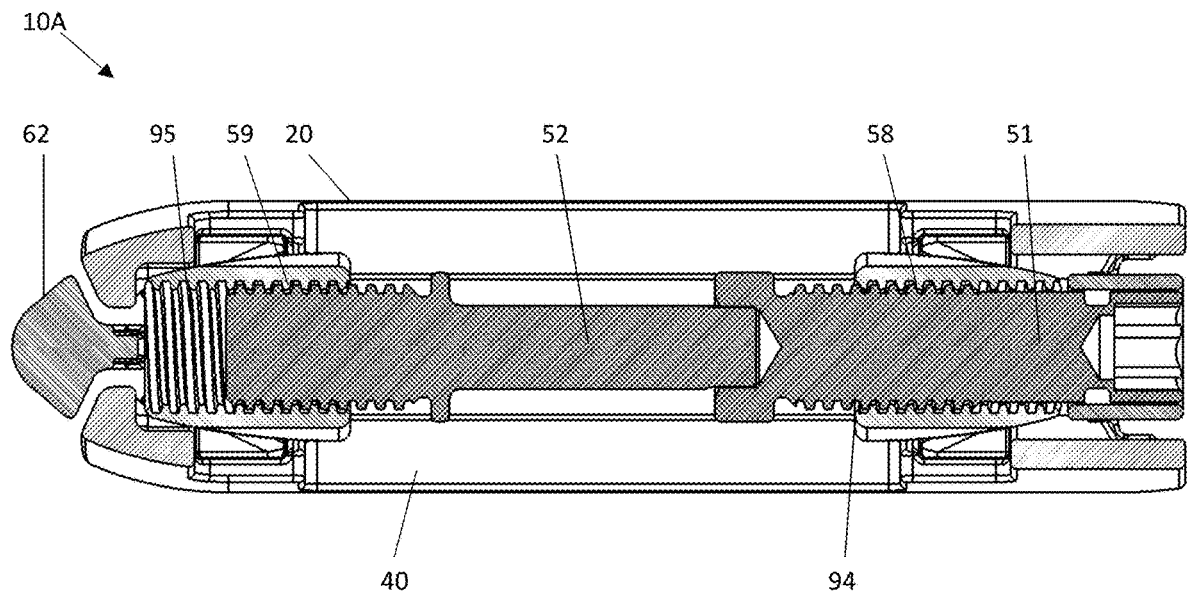

With reference to FIG. 11A, the device 10A in the contracted position is shown in cross section. In FIG. 11B, the device 10A is shown in cross section in the expanded position.

Figure 12A:
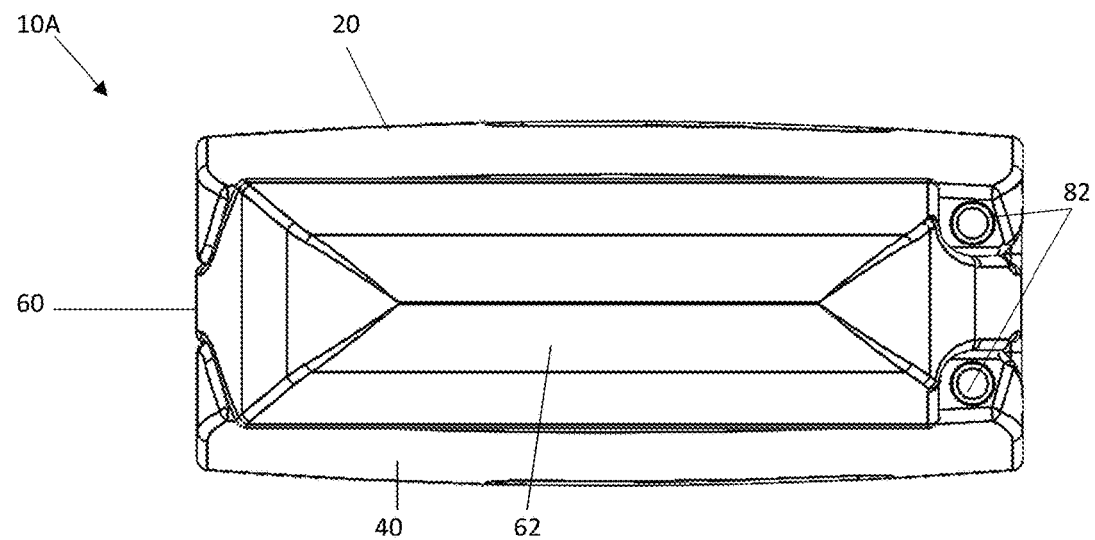
FIGS. 12A and 12B are distal end views, 12A shown contracted and 12B shown expanded.
Figure 12B:
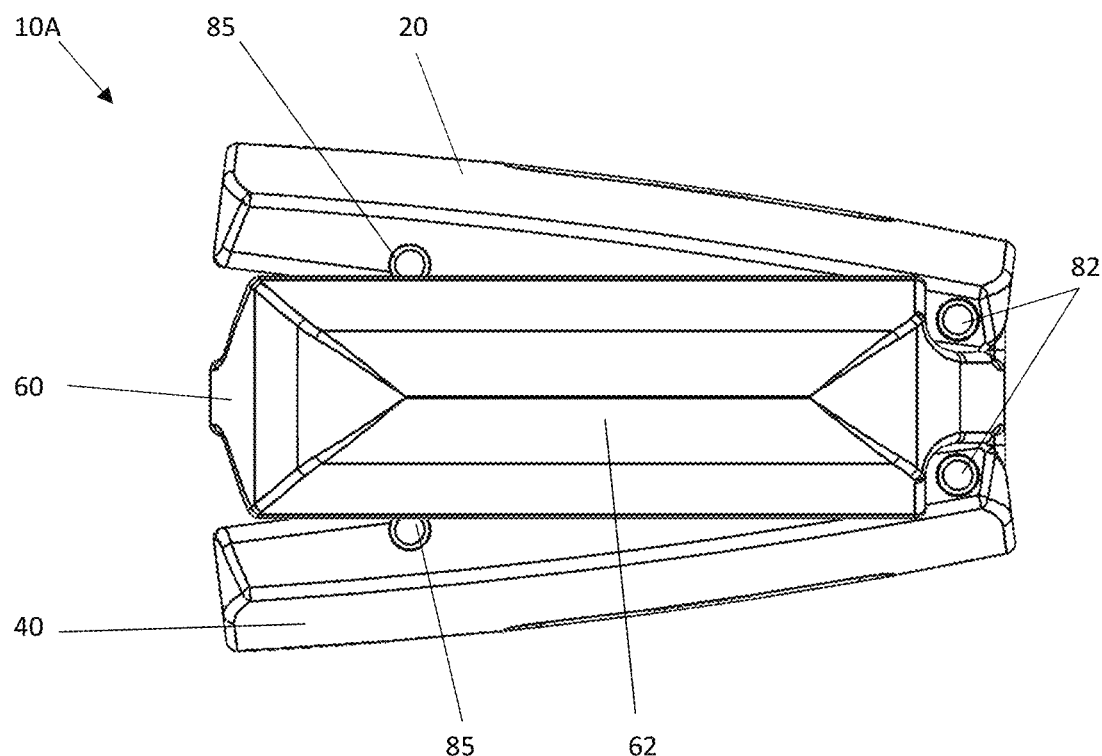

FIG. 12A shows a front view of the device 10A showing the distal end 62 and clearly showing the hinge pins 82 on the hinged side of the device 10A. FIG. 12B is the same frontal view showing the distal end 62 with the base plates 20, 40 shown in the expanded position.

Figure 13A:
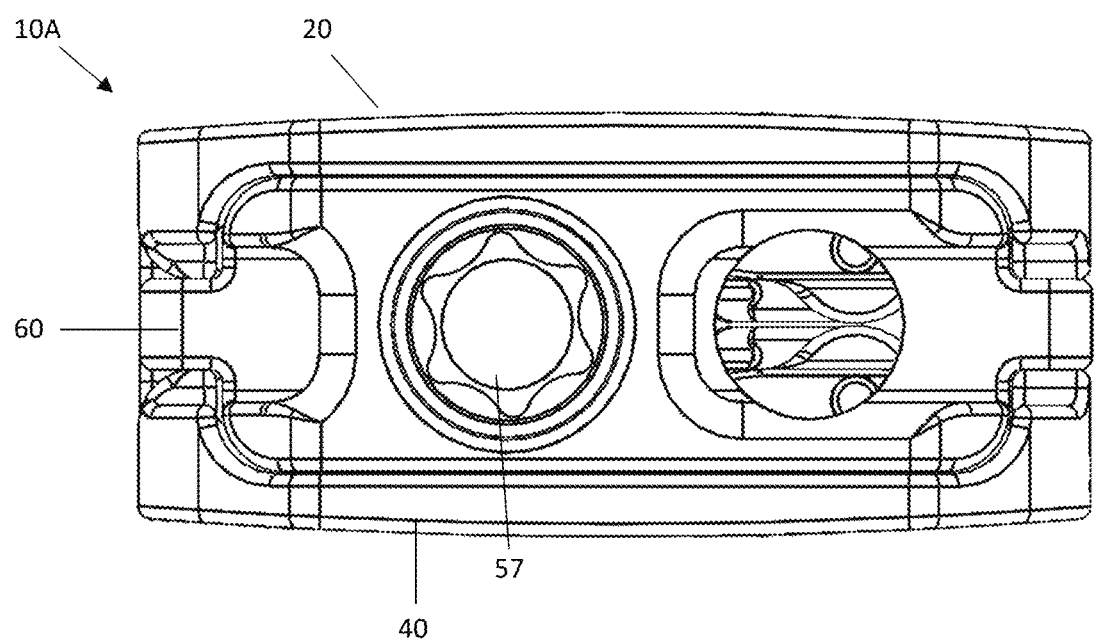
FIGS. 13A and 13B are proximal end views, 13A shown contracted and 13B shown expanded.
Figure 13B:
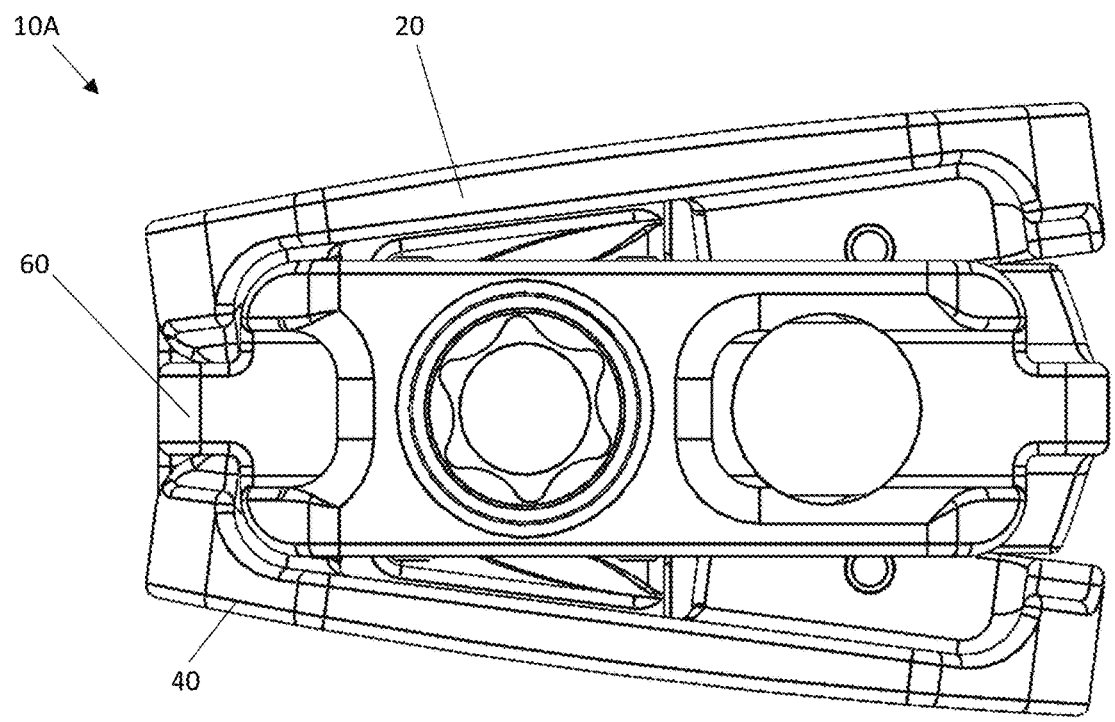

FIG. 13A shows the proximal end of the device 10A, as shown the proximal end of the device has a torque driving element 57 to which a torque driving insertion tool can be inserted to move the drive shaft 50. The torque driving element 57 provides the ability to rotate the drive shaft 50 to expand or contract the device. When doing so, a torque driving insertion tool is inserted into the torque driving element 57 to engage the drive shaft 50 and provide rotational movement of the drive shaft 50. When the drive shaft 50 is rotated as shown in FIG. 13B, the device 10A is in the expanded position.

Figure 14A:
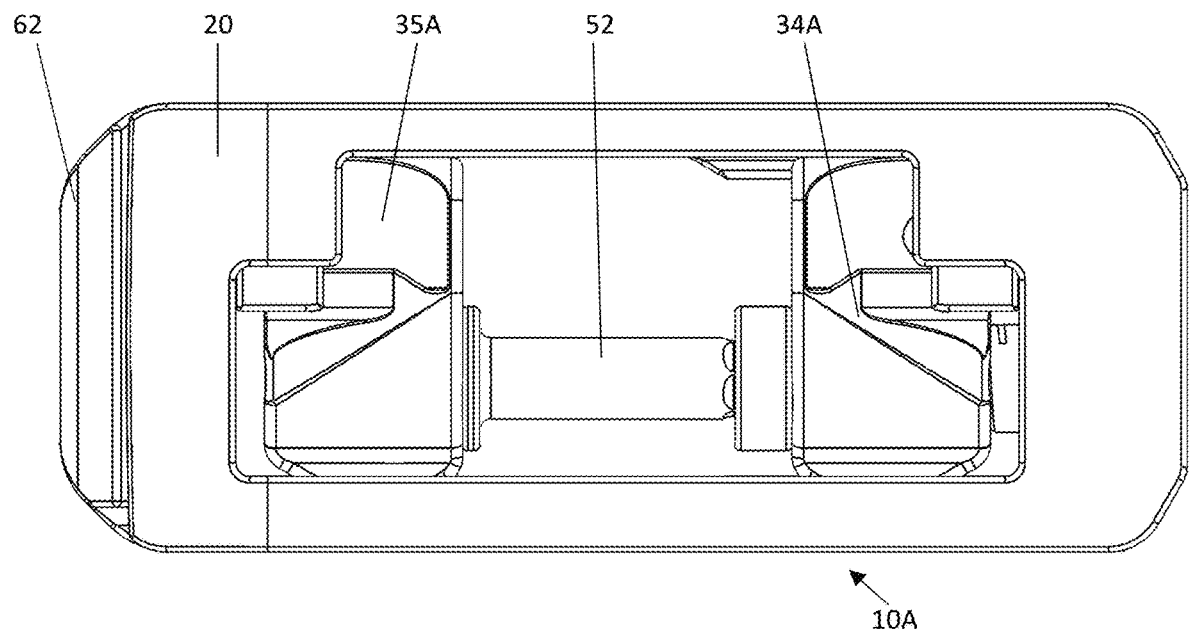
FIGS. 14A and 14B are top views, 14A shown contracted and 14B shown expanded.
Figure 14B:
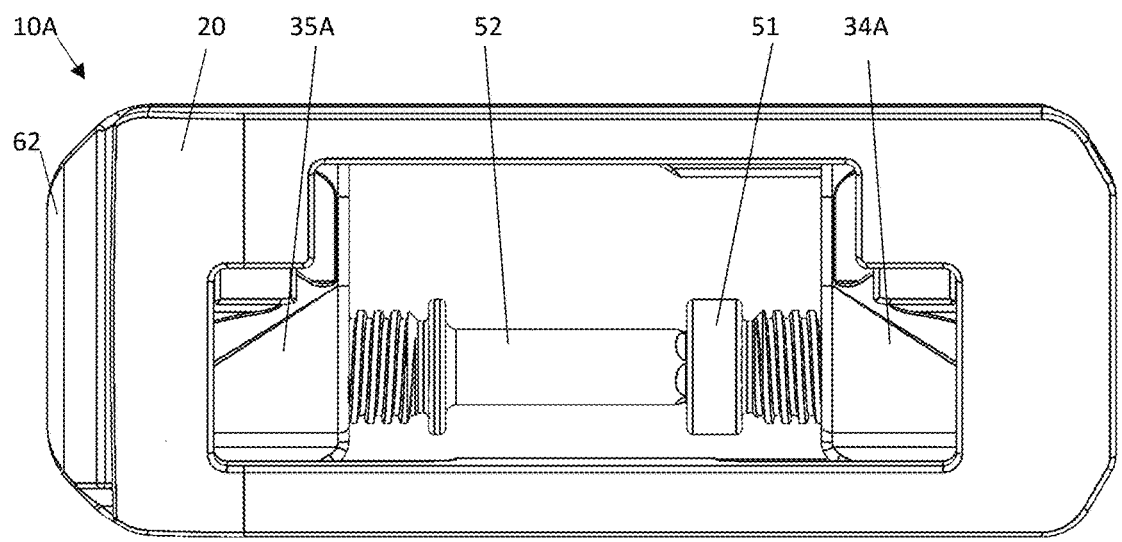

FIG. 14A is a top view of the device 10A shown in the contracted position with the threads 58, 59 not visible when the translating ramps 34, 35 are in the contracted position. FIG. 14B is a top view of the device 10A shown in the expanded position with the threads 58, 59 clearly visible as the translating ramps 34, 35 are moved towards the ends of the device 10A.

In FIG. 15A a cross sectional view is shown wherein it is clearly seen where the translating ramps 34, 35 are positioned relative to the threads 58, 59 of the drive shaft 50. FIG. 15B, when in an expanded position shows the translating ramps 34, 35 are moved towards the ends of the device 10A.

Interestingly, as shown, the distal translating ramp 34 at the distal end of the device fully supports the distal drive shaft component 52 and the proximal drive shaft component 51 is pinned to the frame 60 using pins 53. The pins 53 press through the groove 53A in the proximal drive shaft component 51 and are secured in holes 63 passing into the frame 60.

A third alternative embodiment device 10B is illustrated in FIG. 16. This third embodiment 10B has the same elements as the first two embodiments 10, 10A with the exception that only one base plate 20 is provided. In this embodiment 10B, there is only a frame 60. The frame 60 extends between a distal end 62 and a proximal end 61. Attached to the frame 60 is a fixation end plate 41 similar to the fixation end plate 41 attached to the base plate 40. This fixation end plate 41 is configured similar to the fixation end plate 21 of the base plate 20. In this embodiment 10B, the translating ramps 34, 35 only require the upper surface feature and the pivoting hinged ramps 31 of the upper part of the device. In such a case, the base plate 20 will move relative to the frame 60 as in the previous devices, but there is no underlying base plate to move relative to the frame 60 as there is a single base plate. The frame 60 provides the support for a lower adjacent vertebrae and the base plate 20 is used to elevate the upper adjacent vertebrae.

Figure 17:
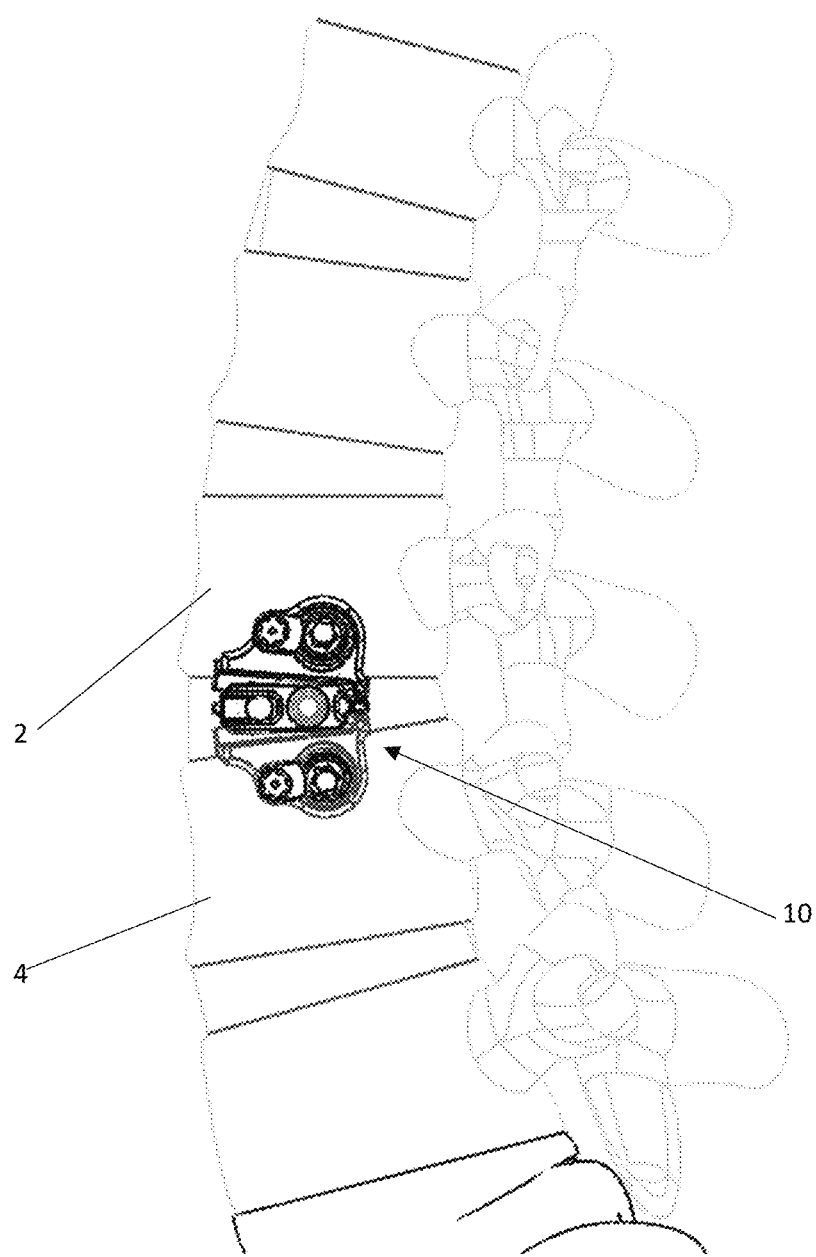
FIG. 17 is an exemplary illustration of the device implanted between two adjacent vertebral bodies.

The device 10 generally is shown inserted within a spine 20 between adjacent vertebrae 2, 4 as illustrated in FIG. 17. The interbody device 10 or 10A is inserted into the intervertebral body disc space in the collapsed state with the base plates parallel to one another so that the tangent planes of the base plates' contoured surfaces are parallel. Another embodiment of the interbody cage is where in the collapsed state the tangent planes of the base plates' contoured surfaces intersect creating a lordotic angle of various values. The expansion/contraction of the anterior side of the interbody is controlled by rotation of the drive shaft screw. As the drive shaft rotates, the ramp assemblies will articulate the base plates by expanding the anterior side of the base plates away from one another by translating the expanding ramps away from the center of the interbody and pivoting the hinged ramps. This operation distracts the spine vertebrae and adjusts the alignment of the spinal column. The drive shaft has built in stops using a shoulder to restrict movement of the expanding ramps towards the center of the interbody once the interbody has fully collapsed. The device is self-locking at any state allowing complete freedom for anterior height/angle adjustment. The fixation end plates incorporated into the base plates accept screws to fixate the interbody device to the superior and interior spine vertebrae. The locking tabs on the fixation end plates are rotated to introduce a flat surface over the top of the screw holes to prevent the screws from being removed from the fixation end plates and vertebral bodies.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An expandable interbody fusion implant device comprising:
  a frame having a first lateral side, a second lateral side, a distal end, and a proximal end;
  a distal ramp assembly and a proximal ramp assembly, each having a translating ramp with a threaded opening and at least one pivoting hinged ramp;
  a first overlying base plate disposed between the distal end and the proximal end of the frame and hinged to the first lateral side of the frame, the first overlying base plate being hinged to the distal ramp assembly at a first of the at least one pivoting hinged ramp, the first overlying base plate being hinged to the proximal ramp assembly at a second of the at least one pivoting hinged ramp;
  a second overlying base plate disposed between the distal end and the proximal end of the frame and hinged to the first lateral side of the frame, the second overlying base plate being hinged to the distal ramp assembly at a third of the at least one pivoting hinged ramp, the second overlying base plate being hinged to the proximal ramp assembly at a fourth of the at least one pivoting hinged ramp;
  a drive shaft, the drive shaft having a distal drive shaft component having threads for translating the distal ramp assembly and a proximal drive shaft component having threads for translating the proximal ramp assembly, wherein the distal drive shaft component is coupled to the proximal drive shaft component; and
  wherein rotation of the drive shaft drives the distal ramp assembly and the proximal ramp assembly simultaneously in opposite directions to selectively expand or contract a distance between the first overlying base plate and the second lateral side of the frame.

2. The expandable interbody fusion implant device of claim 1 wherein the translating ramp of the distal ramp assembly has an exterior lift surface contoured to guide and support the at least one pivoting hinged ramp of the distal ramp assembly.

3. The expandable interbody fusion implant device of claim 1 wherein the distal ramp assembly moves directionally toward the distal end of the frame on rotation of the first drive shaft component as the proximal ramp assembly moves directionally toward the proximal end of the frame on rotation of the proximal drive shaft component.

4. The expandable interbody fusion implant device of claim 2 wherein the at least one pivoting hinged ramp of the distal ramp assembly has a bearing support surface complementary to the exterior lift surface of the translating ramp, with each being inclined with a sloped flat feature.

5. The expandable interbody fusion implant device of claim 1 wherein the distal end of the frame has a tapered end configured to facilitate insertion between vertebral bodies.

6. The expandable interbody fusion implant device of claim 1 wherein the first overlying base plate comprises an end plate with a fastener opening for securing the implant device to a vertebral body, wherein the end plate is pivotable relative to the frame.

7. The expandable interbody fusion implant device of claim 6 wherein the end plate comprises a locking tab attached to the end plate, the locking tab being rotatable to cover a portion of the fastener from loosening after being affixed to a vertebral body.

8. The expandable interbody fusion implant device of claim 1 wherein the translating ramp of the distal ramp assembly and the translating ramp of the proximal ramp assembly each comprises a groove slidable over rails on each lateral interior side of the frame.

9. The expandable interbody fusion implant device of claim 1 wherein the first overlying base plate and/or the second overlying base plate comprises depressions or pockets into which the at least one pivoting hinged ramp fit.

10. The expandable interbody fusion implant device of claim 1 wherein rotation of the drive shaft drives the distal ramp assembly and the proximal ramp assembly simultaneously in opposite directions to selectively expand or contract a distance between the first overlying base plate and the second overlying base plate.

11. The expandable interbody fusion implant device of claim 1 wherein the first of the at least one pivoting hinged ramp is dovetailed to key onto the translating ramp of the distal ramp assembly.

\* \* \* \* \*